United States Patent [19]
Bertoncini et al.

[11] Patent Number: 5,114,681
[45] Date of Patent: May 19, 1992

[54] SUPERFUSION APPARATUS

[75] Inventors: Joseph Bertoncini, Gaithersburg; Calvin Kroener; Wayne Cobb, both of Silver Spring; Robert Evans, Damascus, all of Md.

[73] Assignee: Biomedical Research And Development Laboratories, Inc., Gaithersburg, Md.

[21] Appl. No.: 491,717

[22] Filed: Mar. 9, 1990

[51] Int. Cl.$^5$ .......... C12M 1/00; C12M 1/34; C12M 1/02; C12M 1/04
[52] U.S. Cl. .................. 422/111; 422/186.04; 422/65; 422/68.1; 435/173; 435/287; 435/290; 435/316; 435/313
[58] Field of Search .......... 422/110, 111, 186, 186.04, 422/186.1, 186.2, 50, 63, 65, 68.1, 78, 102, 104; 250/328; 435/287, 290, 313, 316, 173

[56] References Cited
U.S. PATENT DOCUMENTS

| | | | |
|---|---|---|---|
| 3,744,216 | 7/1973 | Halloran | 422/5 |
| 4,234,593 | 11/1980 | Matovich | 422/186.04 |
| 4,764,473 | 8/1988 | Matschke et al. | 435/287 |
| 4,765,965 | 8/1988 | Goudy, Jr. | 422/186.04 |
| 4,801,435 | 1/1989 | Tylko | 422/186.04 |
| 4,954,320 | 9/1990 | Birmingham et al. | 422/186.04 |
| 5,007,995 | 4/1991 | Takahasi et al. | 204/299 R |

Primary Examiner—Robert J. Warden
Assistant Examiner—T. A. Trembley
Attorney, Agent, or Firm—Breneman & Georges

[57] ABSTRACT

A superfusion apparatus for the controlled reaction of a sample within a test chamber through controlled exposure to a series of reagents in a set test sequence is provided for electrical or chemical stimulation to determine if a receptor binding compound is an agonist or antagonist. The superfusion apparatus provides a mass production but meticulously controlled sample environment for controlling temperature, quantity and arrangement of reagents and wash fluids to provide a high reproducability of results which may be compuer assisted. The device has a fully automated mode or a manually operated mode. The fully automated mode allows for the storage and execution of a number of different tests to be performed on the samples due to the provision of desired sequences of test parameters.

20 Claims, 49 Drawing Sheets

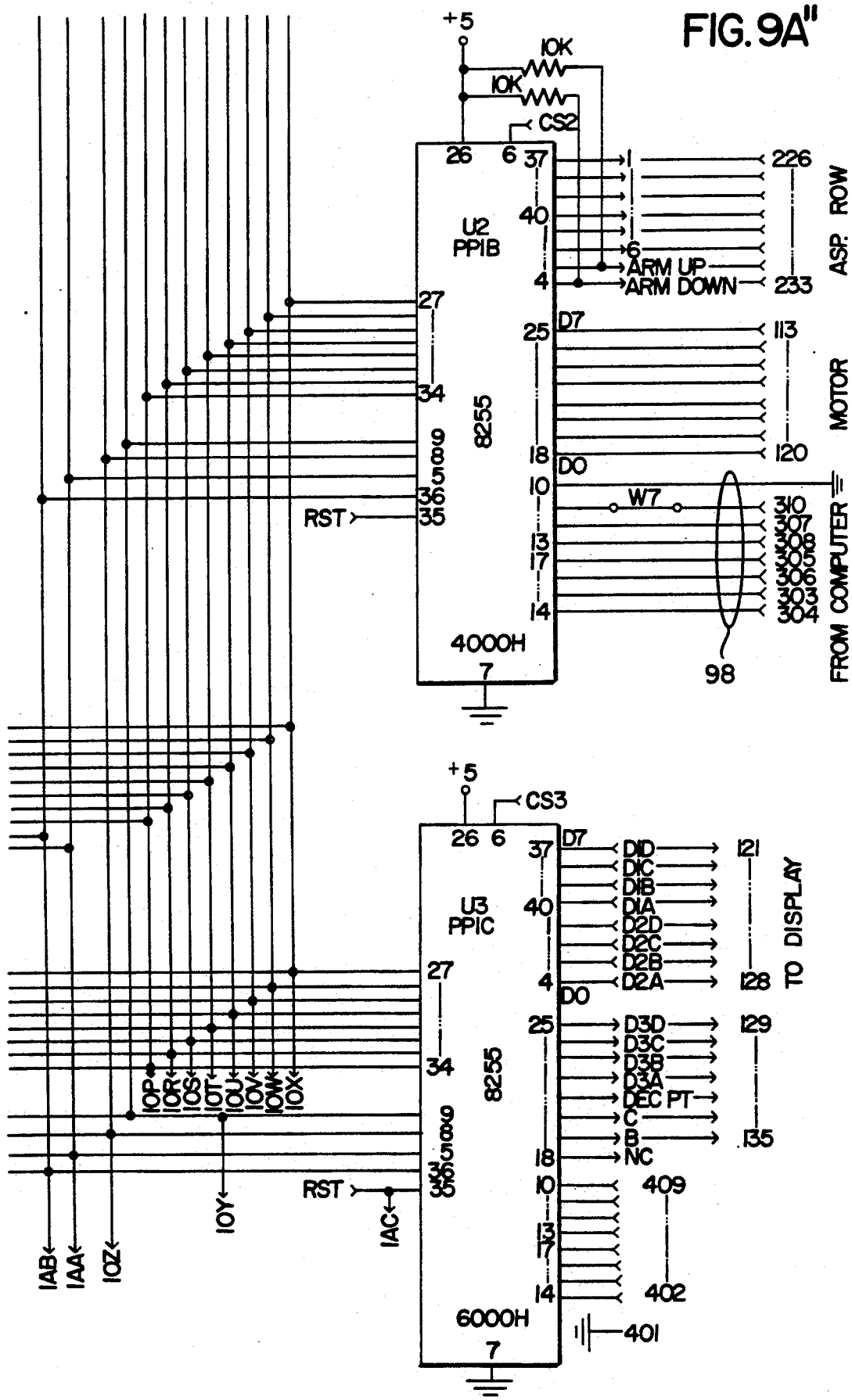
FIG. 9A"

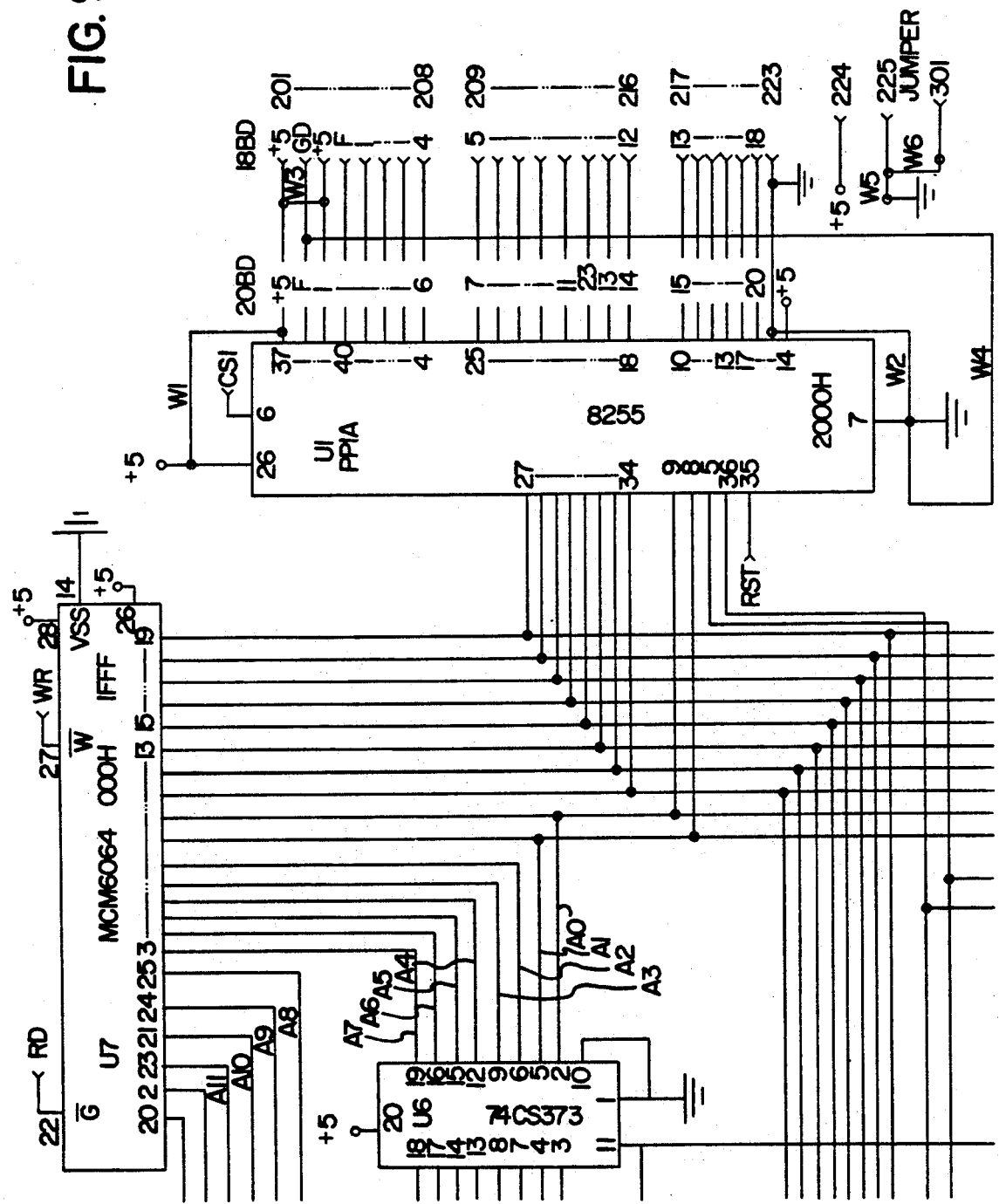
FIG. 9B"

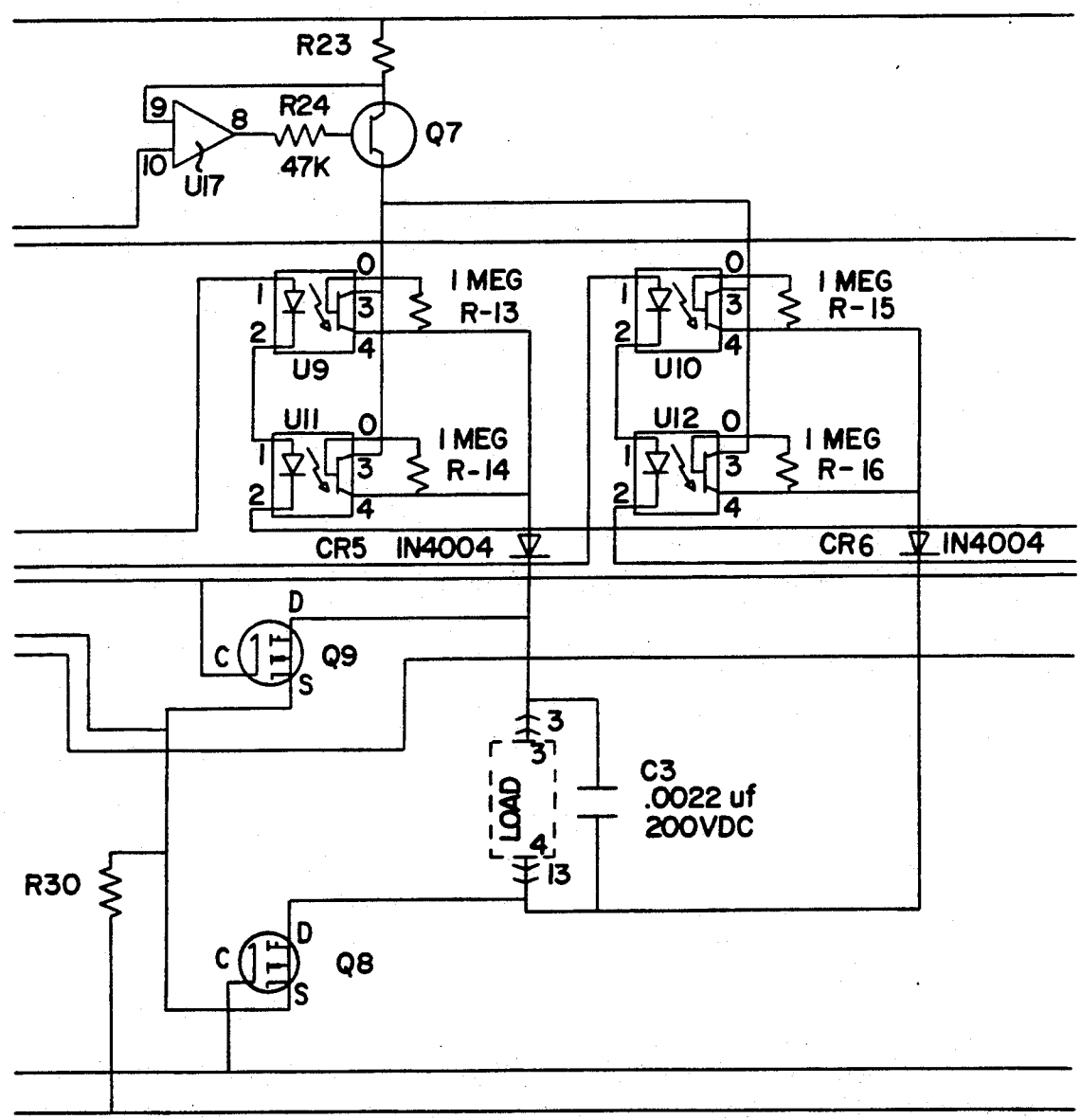
FIG. IIC

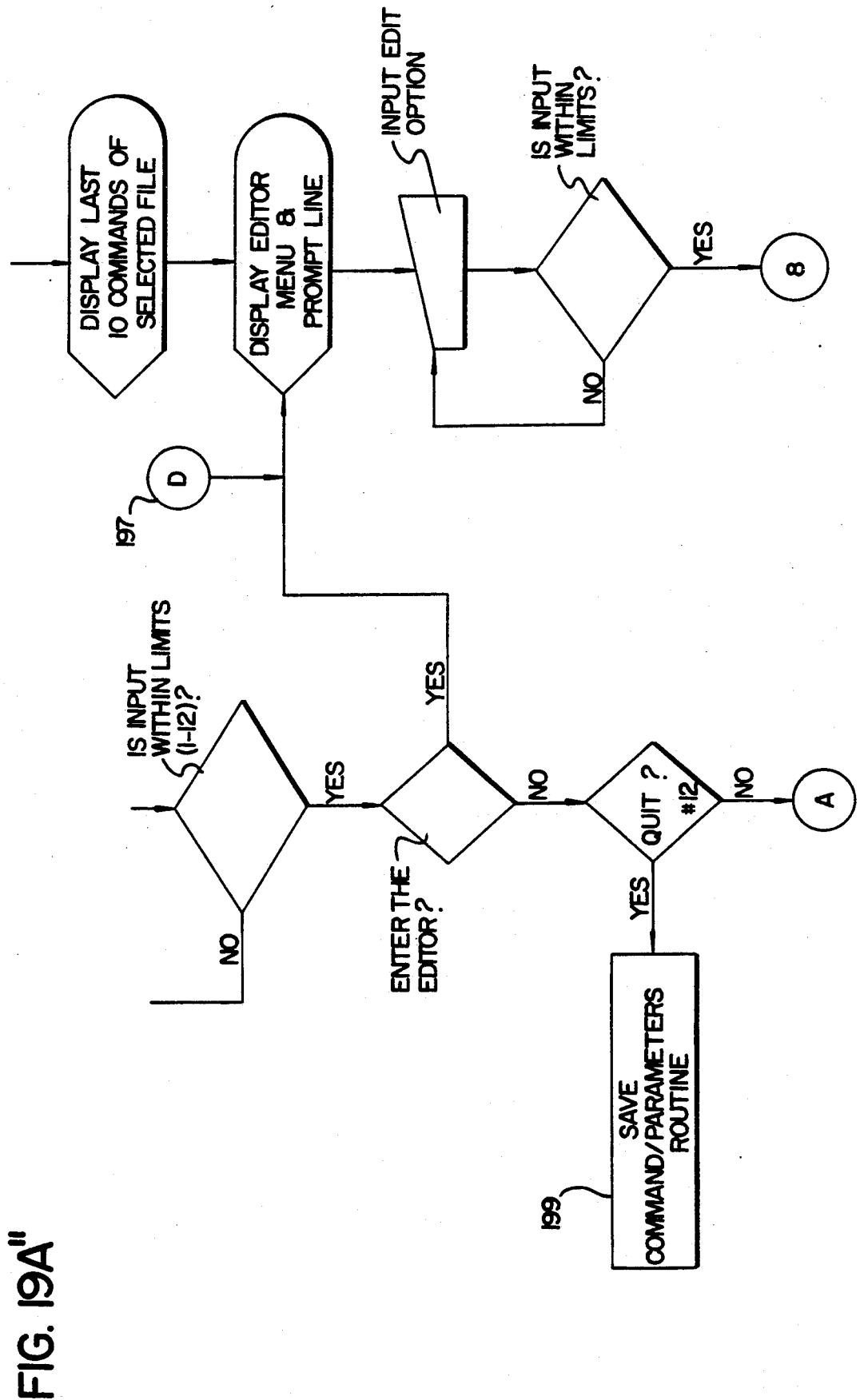
FIG. 19A"

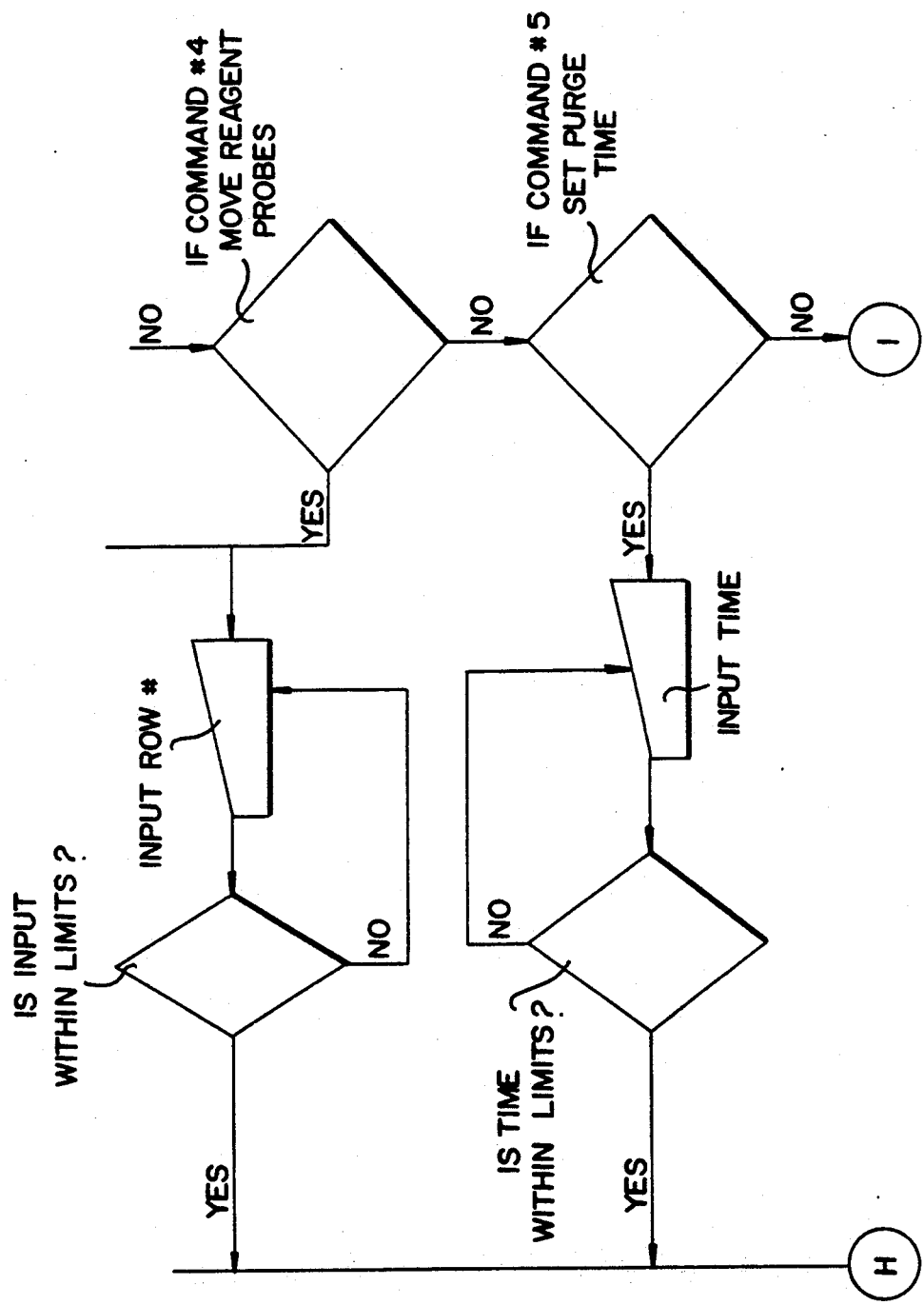
FIG.19B"

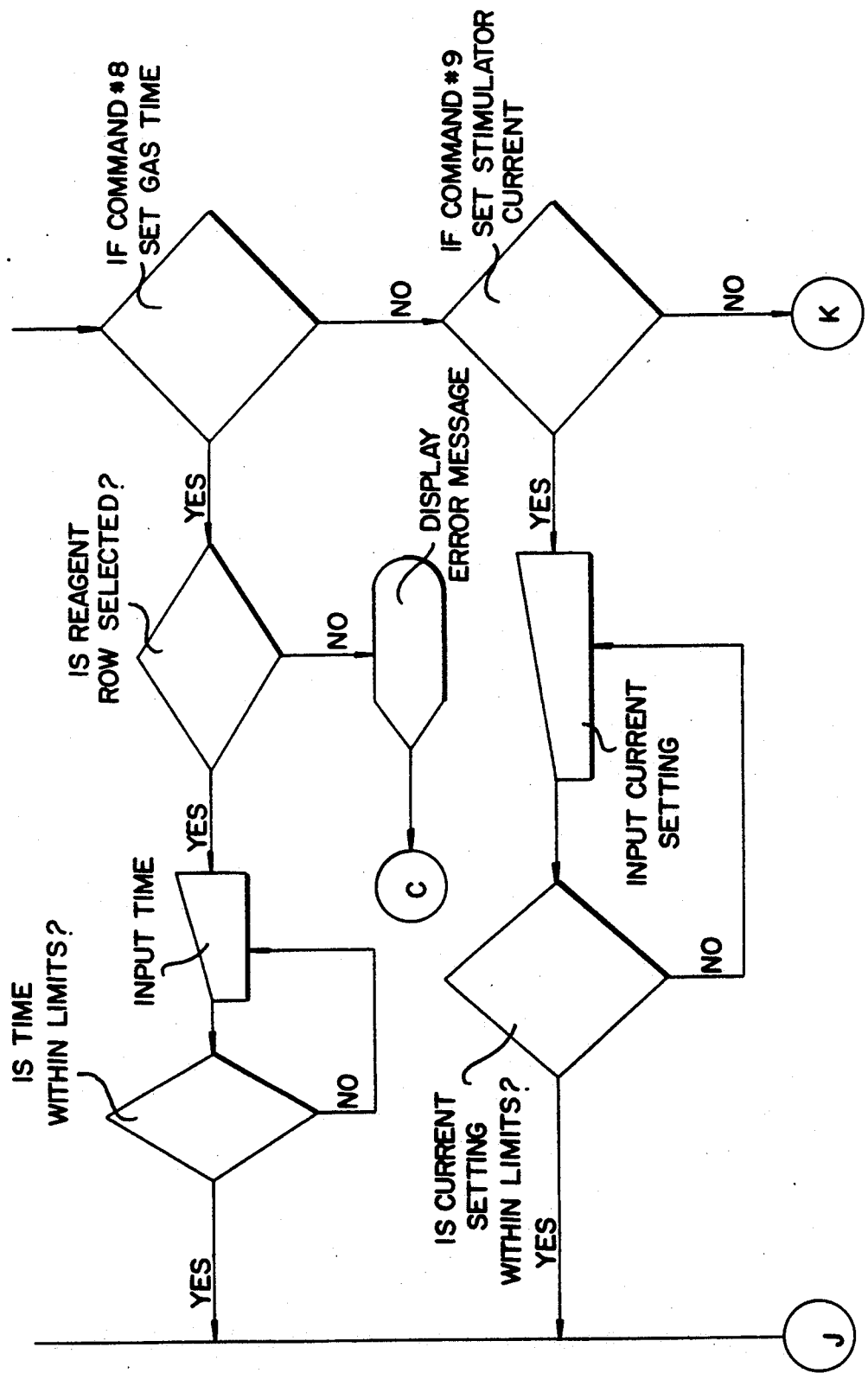
FIG. 19C"

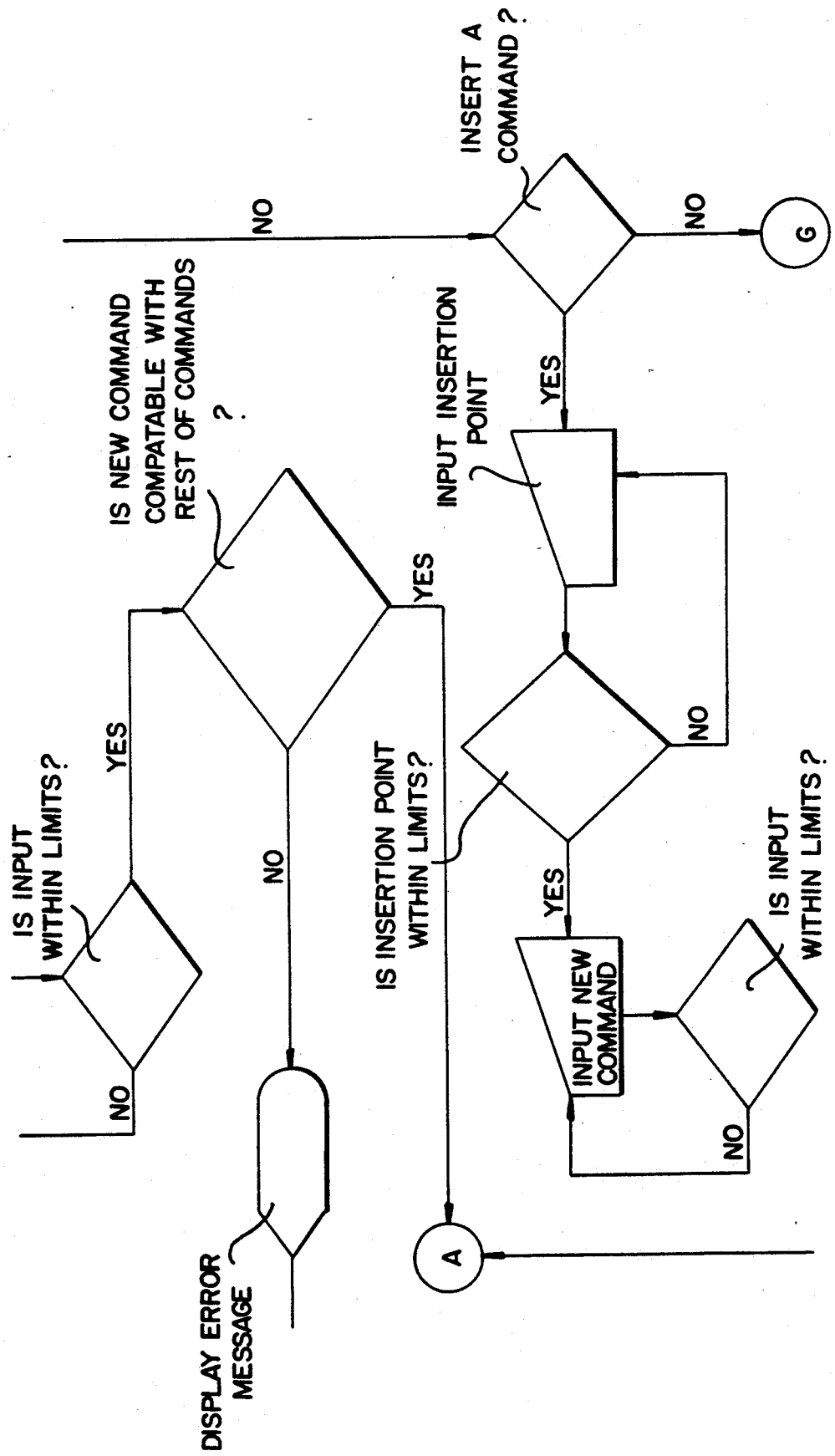
FIG.19E"

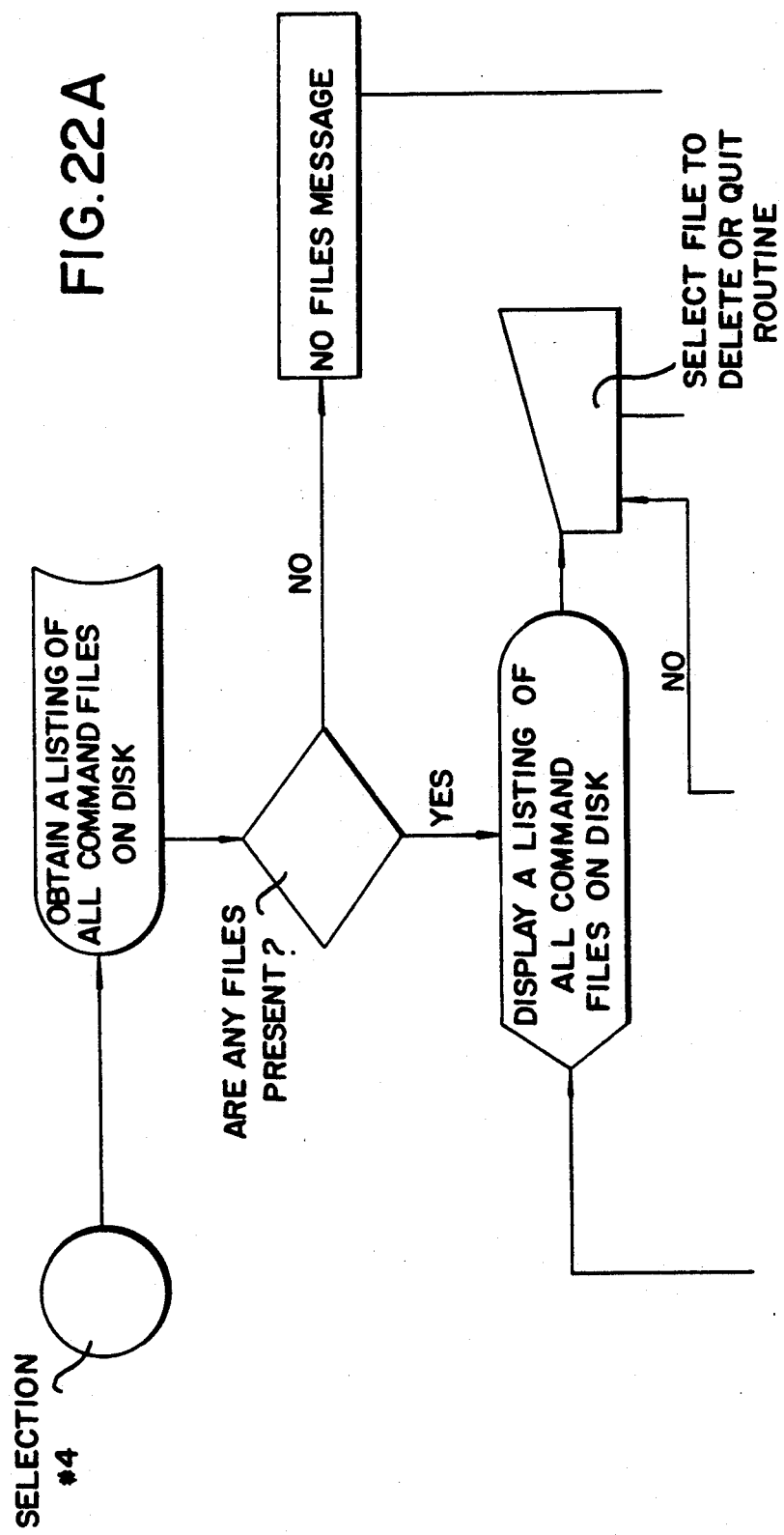

SUPERFUSION APPARATUS

BACKGROUND OF THE INVENTION

The present invention relates to devices for chemical and/or electrical analysis of biological samples. More specifically, the present invention relates to superfusion apparatus for use in a receptor binding procedure and to devices for screening the quality of a binding to discriminate poor bindings from good bindings.

Various devices and procedures are currently utilized for receptor binding procedures, and it is presently possible to obtain data through the utilization of automatic techniques to indicate the binding of a radioactive ligand at a receptor site. While these devices can indicate the occurrence of a binding, they have heretofore been cumbersome and dependent upon the skill of the operator or technician to discriminate the quality of the binding achieved. The lack of a quality uniformity and the differences in chemical and electrical stimulation procedures renders it difficult to discriminate or screen good quality bindings from poor quality bindings, making it difficult to limit further testing to good quality bindings and to exclude poor quality bindings from further testing.

The manual perfusion techniques exist for qualitative analysis of biological samples, however, manual perfusion of multiple samples is both technically difficult and extremely time-consuming and even more dependent upon the skill of the laboratory researcher in determining the results of binding studies. This is particularly evident in the differences in procedures in chemical and electrical binding protocols.

SUMMARY OF THE INVENTION

It is an object of the present invention to provide a superfusion apparatus for use in receptor binding procedures providing a higher degree of control features amenable to both chemical and electrical procedures for determining the binding of a radioactive ligand at a receptor site with a high degree of reproduceability to assess the quality of the resultant binding.

It is a further object of the present invention to provide a superfusion device with simultaneous multiple binding capability which can discriminate between acceptable and unacceptable bindings through the utilization of chemical and/or electrical stimulation.

It is another object of the present invention to provide a superfusion device for use in receptor binding procedures which can evaluate the quality of the bond produced utilizing chemical and/or electrical stimulation.

It is still another object of the present invention to provide a superfusion device which can simultaneously perfuse a multiplicity of tissues with a selective variety of a number of different reactants.

It is yet a further object of the present invention to provide a superfusion device which can simultaneously perfuse a multiplicity of tissues with a variety of reagents in a preselected specified sequence.

It is another object of the present invention to provide a highly automated multichannel, multicell superfusion device with multiple simultaneous perfusion capabilities which provides for acquisition of a multitude of separate effluents corresponding to each perfusion site with minute quantities of reagents precisely controlled utilizing automated procedures.

These and other objects of the present invention are accomplished by providing a superfusion device of multiple channel design which allows for simultaneous perfusion of a number of tissues with any one or a multiplicity of a selected number of reagents. The device allows for an automated and computer controlled superfusion apparatus for the controlled and selected sequencing of the introduction of reactants in the perfusion operation. Further, the device provides for the collection of separate effluents for each perfused tissue sample and further allows for the choice of either chemical and/or electrical stimulation of the perfusion site.

By providing a novel reaction chamber including a tissue chamber which is provided with a thermal jacket for temperature control and controlled ports for injection of reactants and with electrical stimulation terminals, the above and other objects of the present invention with the desired effect of creating a controlled repeatable and evaluable perfusion reaction can be accomplished.

The device of the present invention is amenable to computer control for fully automated operation while still providing for manual intervention to allow for a wide variety of laboratory test procedures and parameters. The device of the present invention allows for fully automated operation for a large number of samples for automated test procedures or a small number of samples with the ability to preselect all test parameters to ensure appropriate repeatable test conditions. The device allows for quality determination of receptor binding to assess acceptability by appropriate screening through specified, desired sequences by providing for the appropriate introduction of reactants and proper collection of effluents.

BRIEF DESCRIPTION OF THE DRAWINGS

For a better understanding of the nature of the present invention, reference is made to the following figures and detailed description, wherein like elements have generally been accorded like reference numerals, and wherein.

DETAILED DESCRIPTION OF PREFERRED EXEMPLARY EMBODIMENTS

Figure 1:
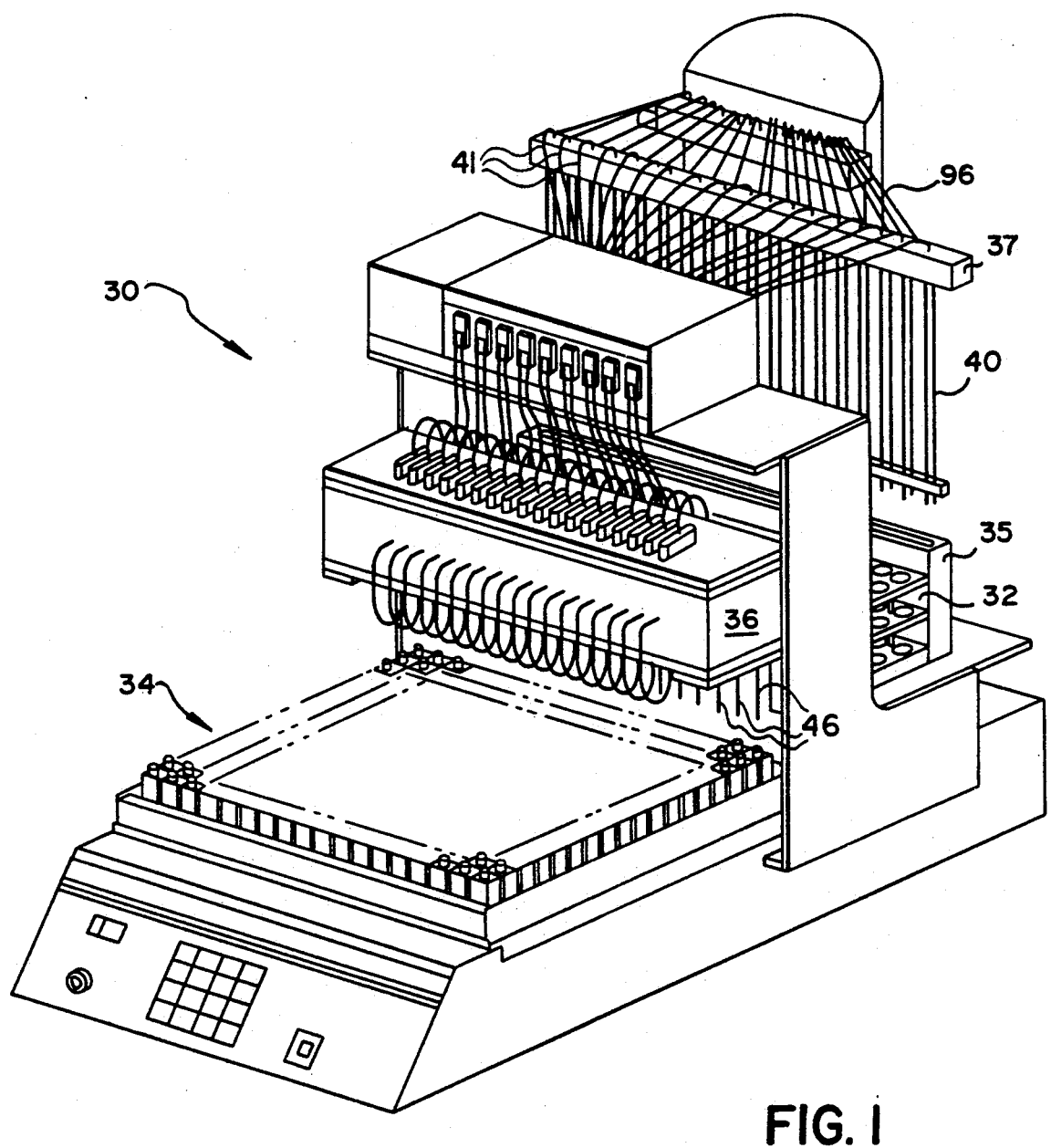
FIG. 1 is a front perspective overall view of a perfusion device constructed in accordance with the invention.
Figure 2:
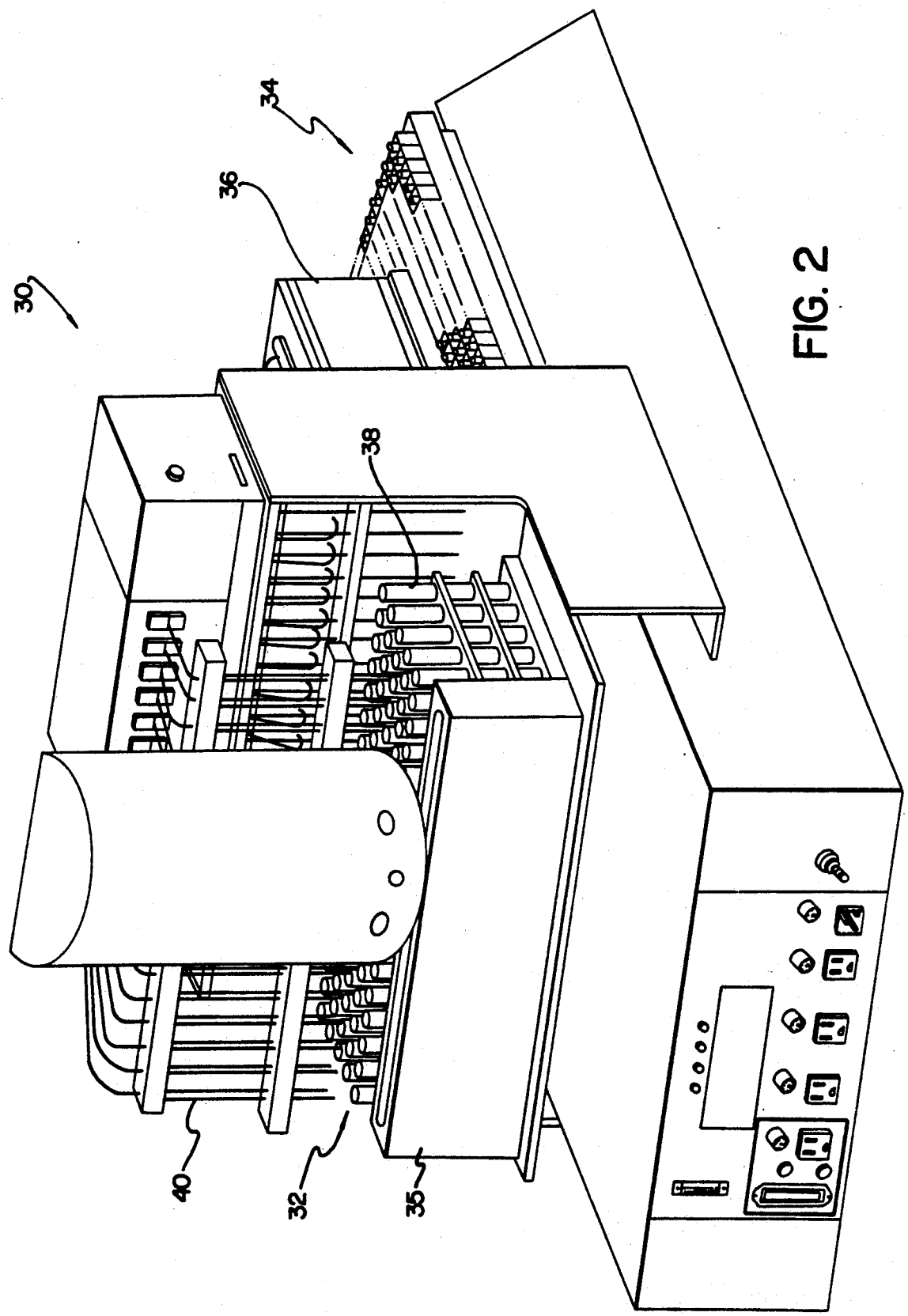
FIG. 2 is a rear perspective overall view of the perfusion device of FIG. 1.
Figure 3:
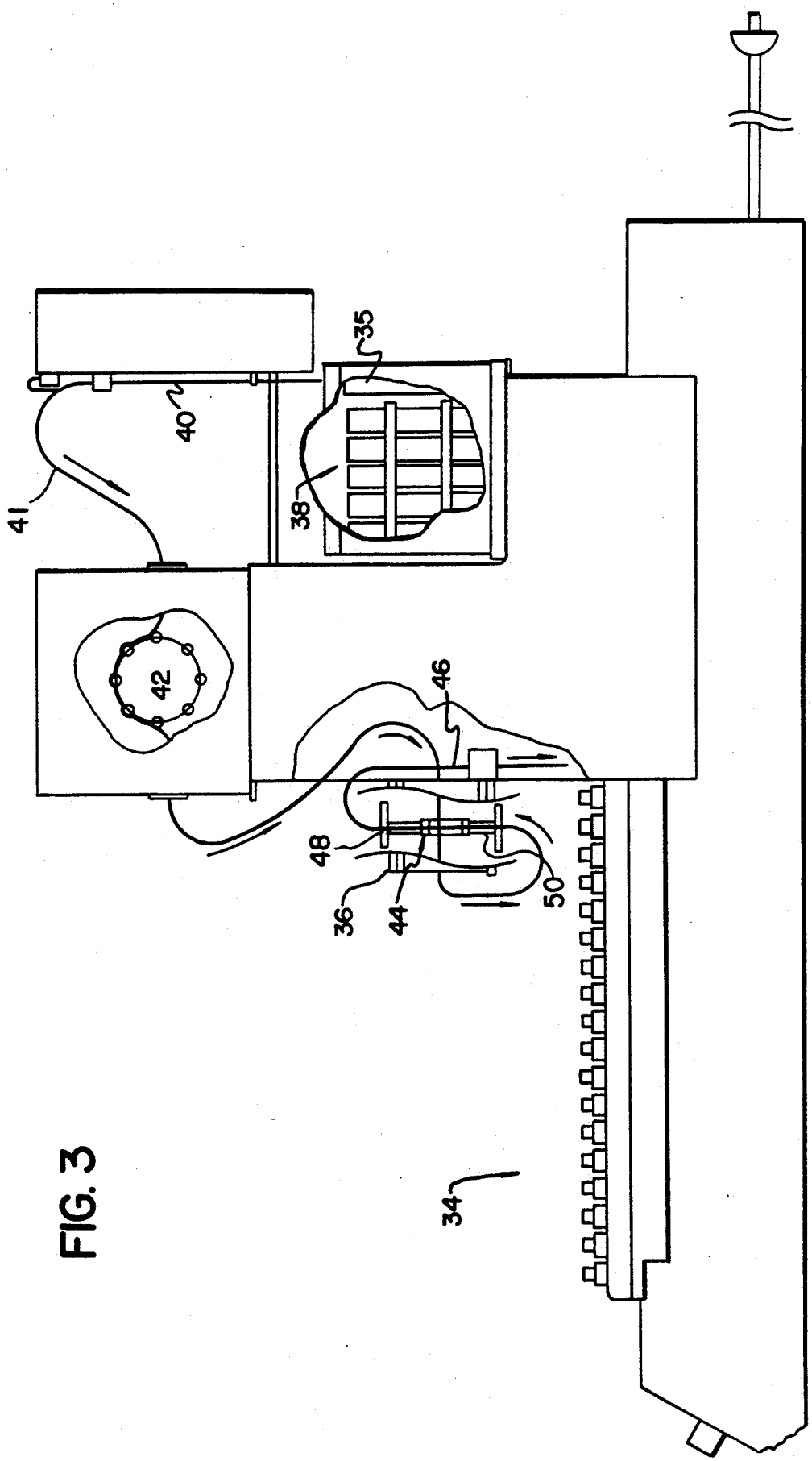
FIG. 3 is a schematic view diagramming the flow through the perfusion machine.
Figure 6B:
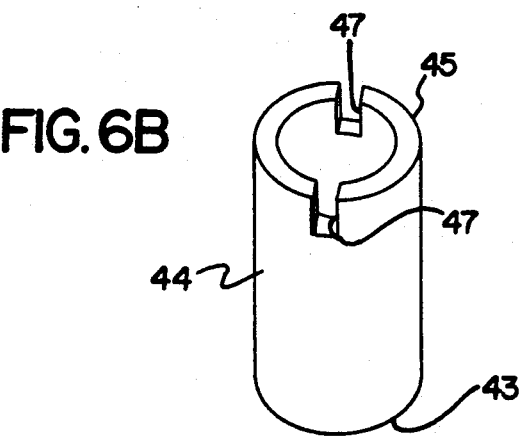
FIG. 6B is a perspective view of a sample reaction chamber constructed in accordance with the preferred embodiment of the invention.

As illustrated in FIGS. 1, 2 and 3, the superfusion device 30 includes a rack of aspiration tubes 32 in the rear of the machine from which various reagents and/or wash solutions can be withdrawn and a rack of delivery tubes 34 in the front portion of the machine for receiving effluents from the reaction chambers within the reaction chamber block 36. In the preferred application five rows of twenty test tubes per row are provided by the rack of aspiration tubes 32 (FIG. 2) or by a common reagent vessel (not shown) in which each test tube 38 is accessed by a separate pick up tube 40, each of which tube supplies reagent to a particular sample through separate peristaltic pump tubing 41 controlled by a common peristaltic pump 42. The overall flow of the device is illustrated in FIG. 3. Reagents or wash solutions are withdrawn as desired manually or automatically through computer control from one of the test tubes 38 within the rack of aspiration tubes 32 up through pick up tube 40 by means of pump 42 for delivery into a desired reaction chamber 44 within reaction chamber block 36. Reaction or tissue chamber 44 is preferably made of polyethylene or some other semi elastic material for conforming and being held in place by O-rings 58 and 60 around upper plug 48 and lower plug 50 and 50. Chamber 44 may be cylindrical at both ends like end 43 of chamber 44 or in the preferred embodiment be notched at one or both adjacent sides of end 45 (FIG. 6B). One or more notches 47 at one end of chamber 44 makes certain that the plug 48 and 50 are pulled apart chamber 44 with the tissue sample will remain with the plug in contact with the notches 47. The flow of reagents through reaction or tissue chamber 44 is better illustrated in FIGS. 5, 6A, 6B and 7B and will be described in greater detail below. After passing through the reaction chamber 44, the effluents of the chamber pass out delivery tube 46 and into an appropriate one of the test tubes in the rack of delivery tubes 34 as illustrated in FIG. 3.

Both the aspiration tubes rack 32 and the delivery tubes rack 34 can be articulated back and fort to maneuver the appropriate tube below the pick up tube 40 or the delivery 46 tube receptively. In this manner, a desired reagent can be effectively delivered to a specific reaction chamber 44 within the block 36; and effluents of a specific chamber can be collected as desired into a selected tube in the delivery rack 34.

Preferably pump 42 is of the peristaltic pump type to provide for smooth flow of reagents into the reaction chambers. A separate peristaltic pump tubing 41 is provided for each chamber so that the chambers can be independently fed. Control for each of the peristaltic pump tubing is provided by a common peristaltic pump 42 by varying the speed of the peristaltic pump motor through the automated control mechanisms described below. The peristaltic pump 42 preferably includes variable speed so as to be capable of providing the desired reactants and/or reagents at a specified delivery rate. The requirements of a block having an array of a 20 reaction chambered superfusion device can be satisfied with a 20 channel Nanostat peristaltic pump which provides for independent control of each of the 20 channels with modified circuitry for adaptation to utilization in the automated and computer controlled applications of the superfusion device of the invention.

The aspiration for delivery to rack 32 includes five rows of independent test tubes for holding selected reagents and a final sixth row occupied across the length of the rack 32 by a common reagent vessel. In such operations a common reagent vessel 35 is typically filled with a wash solution for flushing the reaction chambers 44 as necessary or desired.

Figure 7B:
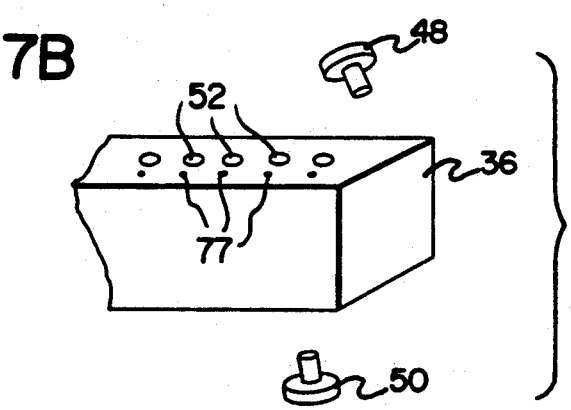
FIG. 7B is a schematic illustration of a portion of a reaction block housing including a plurality of reactive chambers with an associated cooling jacket.
Figure 5:
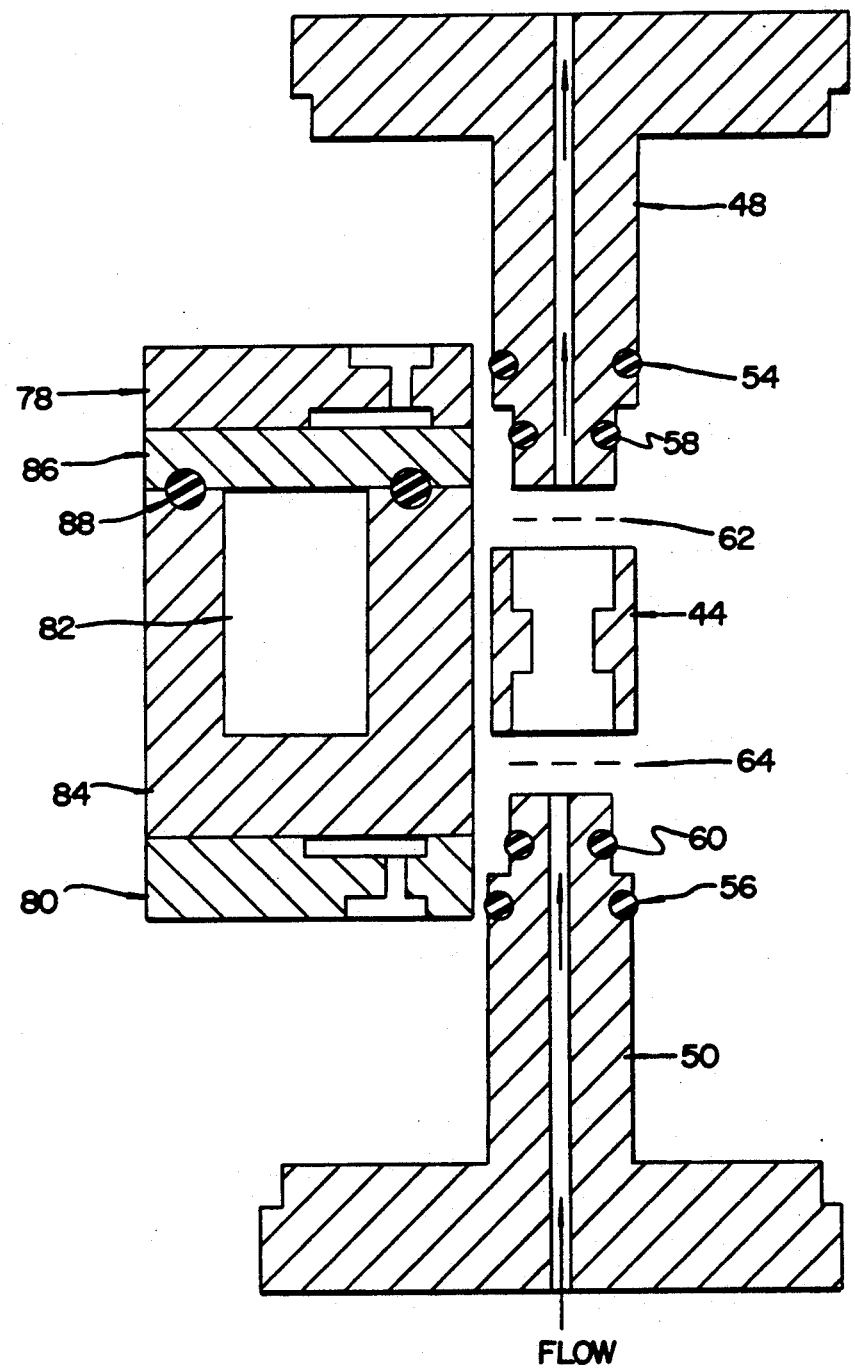
FIG. 5 is an exploded cross sectional assembly view of a reaction chamber for chemical stimulation without means for electrical stimulation.
Figure 6A:
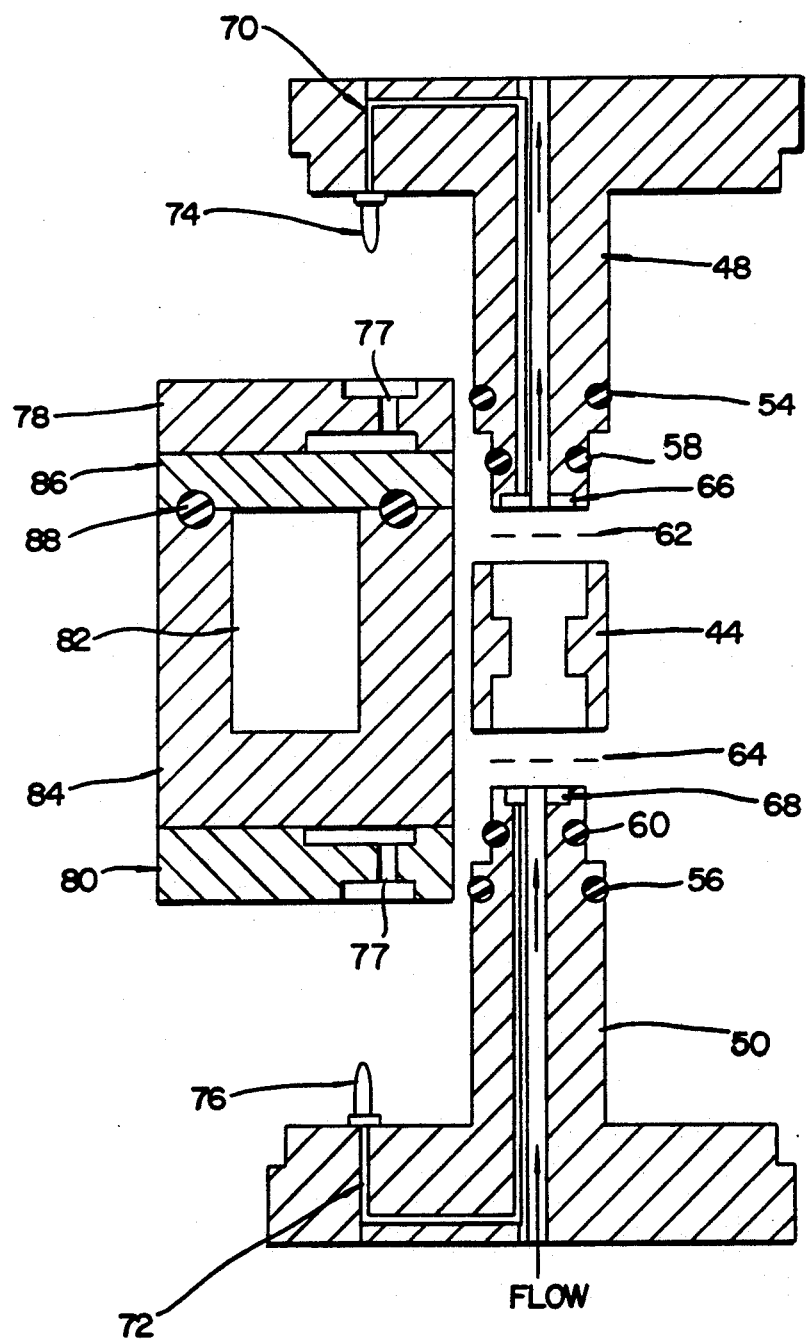
FIG. 6A is an exploded cross sectional assembly view of a reaction chamber with provision for electrical stimulation.
Figure 7A:
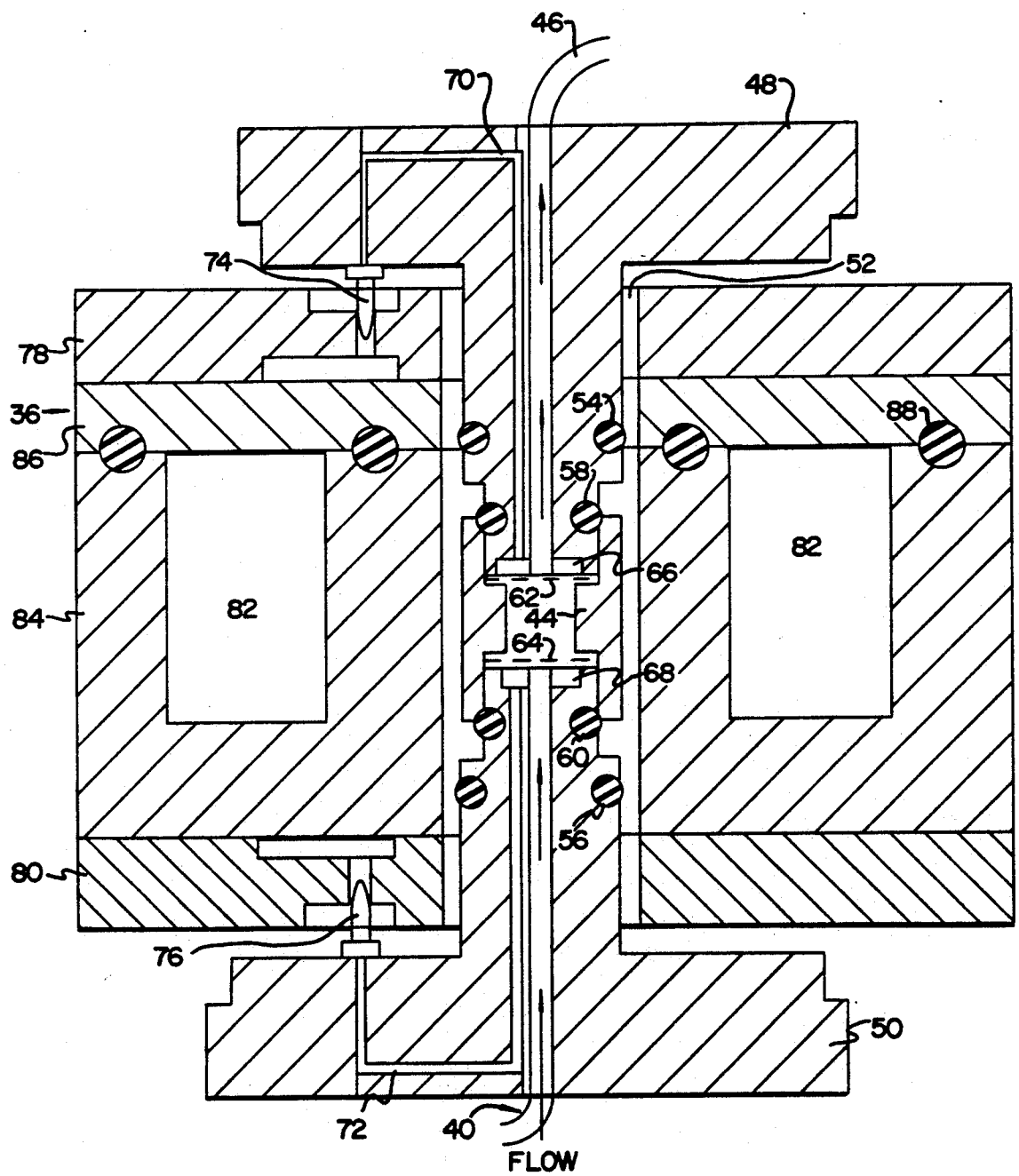
FIG. 7A is a cross sectional view of a reaction chamber and associated cooling jackets.

As illustrated in FIGS. 7A and B, upper plug 48 and lower plug 50 fit into either end of a channel 52 through the reaction chamber block 36. Each of the plugs 48 and 50 are provided with an "O" ring 54 and 56, respectively, to seal the plugs to the inside of the channel 52 within chamber block 36. Further, the plugs 48 and 50 are provided with "O" rings 58 and 60, respectively, for sealing the end of each plug member into the reaction or tissue chamber 44. In this manner, reagents or other fluids entering plug 50 through tube 40 will flow in a controlled manner through reaction chamber 44 out through plug 48 and into exit tube 46. The reagents or other fluids will flow through filter papers 62 and 64 if provided, as well as reacting with any tissues contained within chamber 44.

As illustrated in FIGS. 6 and 7, each of plugs 48 and 50 can be provided with platinum foil electrodes 66 and 68 which are connected by a platinum wire 70 or 72, to a connector 74 or 76, respectively. These connectors 74 and 76 are plugged into connections in the top and bottom simulation banks 78 and 80, respectively, as the plugs 48 and 50 are inserted into channel 52. The connections in the simulation banks 78 and 80 are provided with electrical current as appropriate under computer control within the superfusion device as for electrical stimulation by manual or by automatic computer control means detailed herein below.

As illustrated in FIG. 7B, there are a number of channels 52 and corrections 77 within chamber block 36. In the example illustrated herein, there are 20 such channels within the block 36. One or more of these channels can be fitted with a pair of plugs 48 and 50 which retain an independent reaction chamber 44 therebetween. Further, each of the sets of plugs can be provided with the platinum electrode wire connections described above as desired. In applications where chemical stimulation is desired it is not necessary for the chambers to include the electrical contacts for electrical stimulation capability, but the electrically stimulatable chambers can be used for either or both electrical or chemical stimulation as desired.

Also included within the chamber block 36 is a water cavity 82 which surrounds all of the channels 52 through the chamber block 36. The chamber block 36 includes a main body 84 and a top plate 86 which, when assembled with "O" ring 88 therebetween, forms the water cavity 82. The water cavity 82 acts as a water jacket to maintain a desired temperature within each of the tissue chambers 44. The water chamber is fed by hydraulic connections at one end of the chamber block such that the water flows down the length of the chamber block 36 along one side of the tissue chambers and back down the length of the chamber 36 in the opposite direction along the opposite side of tissue chambers 44 and out of the chamber block 36.

Each of the test chambers 44 within the chamber block 36 is provided with a separate peristaltic pump tubing 41 channel for supplying the reagents to that reaction chamber. Through provision of a multitude of reagent test tubes 38 within the reagent rack 32 and through computer controlled positioning of the tubes 40 for each test chamber, and by activating the appropriate pump 42, the desired reagents can be supplied to one or more desired tissue chambers 44 as necessary. Further, by computer controlled positioning of the test tubes within the delivery tube rack 34, the effluents from the various tissue chambers 44 can be independently and individually collected in a controlled, desired manner. Further, by provision of the computer controlled electrical stimulation, any of the desired tissue chambers can be stimulated by means of the platinum electrodes 66 and 68 to effect the desired test parameters. Easy, rapid and unrestricted switching between chemical and/or electrical can therefore be achieved.

Figure 8:
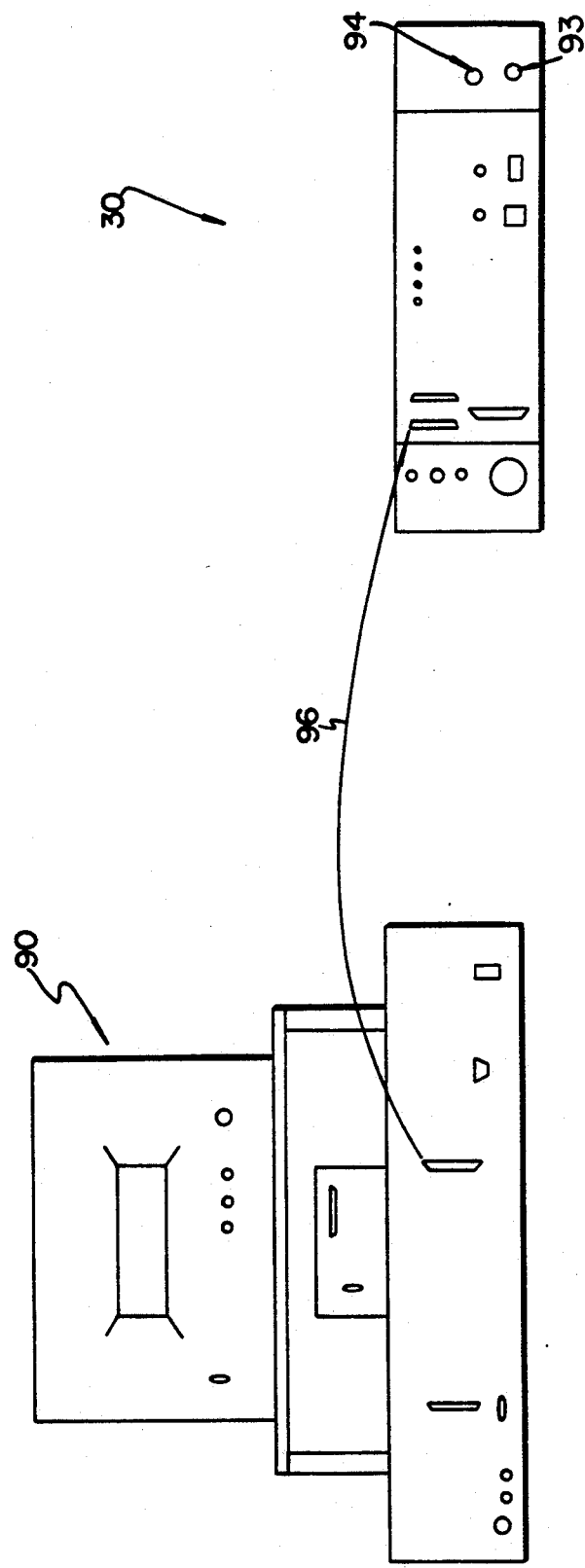
FIG. 8 is a wiring diagram illustrating the interconnection of a computer control and the superfusion unit.

In order to effect the automated control of the perfusion function, the superfusion device 30 can be connected to a computer 90 as illustrated in FIG. 8. The superfusion device 30 is provided with a number of input and output terminals as illustrated in FIG. 8. Appropriate communication cabling 92 is connected between the superfusion device 30 and the computer 90. Positioning of the rack of delivery tubes 34 aspiration tube rack 32, as well as the addition of reagents to individual chambers and the provision of electrical stimulation can be controlled by the computer 90. Further, reagent heating and cooling jacket temperature can be program controlled from the computer 90. A gas inlet 93 and gas outlet 94 are also provided on the back of the superfusion device 30. These inlets can be provided with appropriate gas source and gas evacuation tubes if gassing of the test chambers is desired. As illustrated in FIG. 1, a second gassing tube 96 can be provided for each of the test chambers 44 in order to introduce gas as a reagent into the tissue chambers 44. The flow of gas through the specified gas delivery tubes 96 can also be automated and controlled by the computer 90.

In operation, the logical flow of the automated operation, as illustrated in the flow diagrams of FIGS. 18-24, is as follows. The automated system will offer the programmer or automater the following selections when establishing automated testing parameters:
1. Create and Save Test Parameters
2. Modify Test Parameters
3. View/Print Test Parameters
4. Delete a Test File
5. Run a Test
6. Quit Program This allows the programmer to fully automate any desired test parameters, including reagent sequencing, electrical stimulation, gassing, effluent collection, cell preparation and/or fluid flushing.

The superfusion device provides numerous advantages over traditional binding protocols by simulating the extracellular environment using physiological buffers and gases that continuously flow past tissue sections, cultured cells or synaptosomes. The superfusion apparatus of the invention can be utilized for chemical stimulation or for electrical stimulation which electrical stimulation can be used to explore neurotransmitter release which does not occur in binding protocols.

Changes in conditions (pH, ions, gases) can be assessed in the same tissue chamber and this is a distinct advantage over binding assays where only one condition can be explored per tube.

The superfusion technique can be used in conjunction with receptor binding techniques to fully evaluate secondary events such as neurotransmitter release and second messenger events. The method of superfusion is as easy to use as binding techniques and the computer-driven machine makes the process convenient.

In the "Create and Save Test Parameters" mode, FIGS. 19A-19F, the programmer can establish the desired test parameters. The desired parameters can be saved for future retrieval so that repetitive tests can be duplicated at different times with a high degree of replication and comparative accuracy.

A number of standard variables are presented for selection by the individual establishing the automated test routine. The selected parameters are then verified for accuracy and acceptability to determine if the desired sequence of testing can be executed by the superfusion device. If the specified test parameters are appropriate, the specified test is named and saved for repetitive use as desired.

The automater must select a number of test parameters for each of the reaction chambers of the superfusion device, such as the twenty individual chambers 44 illustrated herein. For each chamber, the automater must select the first aspirate or reactant from one of the rows 1-6 of the aspiration tube rack 32. An aspiration time in minutes and seconds must then be selected and the automater must indicate whether or not electrical stimulation should occur during this aspiration. The speed of the pump can be selected for the chambers.

The reagent row, the aspiration time, pump speed and the desirability of electrical stimulation can be provided for each aspiration interval. The effluents from each aspiration interval are collected in the appropriate row of vials in the delivery tube rack 34 corresponding to that aspiration interval (i.e. first aspiration interval is collected in the first aspiration row, the nth aspiration interval collected in the nth row).

Data once established can be reviewed before execution by the automated superfusion device. In the example illustrated herein, the review consists of a display of each of the chambers and the indicated aspiration reagent selections for each of the aspiration cycles of the established test parameters. The test can be changed, deleted or added to, to allow precise establishment of desired test parameters.

In the second mode listed above, the test parameters for any saved test can be easily modified through utilization of the automated system. This allows for quick and accurate changes in established test parameters for reconciling test conditions to present requirements, thus eliminating the need to re-establish the test parameters or to reconstruct a manually executed test.

The established test parameters of any testing sequence can be viewed and/or output to a printer if desired. The viewing or printing of the test parameters will provide the selected reagents and their introduction sequence into each of the test chambers utilized.

In order to execute one of the established test sequences, the operator selects the desired test and initiates a test run by the automated system. Prior to running an automated test the operator must establish proper pretest conditions. The appropriate number of reagent and collection vials must be present in both the aspiration rack 32 and the collection rack 34. The proper reagents desired for the particular stimulation test is placed in the appropriate aspiration vials within the aspiration rack 32. The operator must also establish that the proper desired and appropriate tissue samples are present in the appropriate respective reaction chambers 44 and that all chambers and plugs are properly in place. The desired test is then selected and execution begun.

Standard execution is initiated with collection of effluents beginning in the first row of vials of the collection rack 34. However, it is not necessary to start with the first row since the automated system can be programmed to begin at any desired row. This allows for more than one test to be collected in the same rack of collection vials provided ample room exists within the given number of collection vials in the collection rack 34. For example, a first test run which only collects six samples can be run in rows 1-6 of the collection vials in the collection rack 34 and then a second test which utilizes eight vials may be run collecting in vials 7-14 of the twenty rows in the collection rack 34. The number of vial rows needed for a test is dependent upon the number of aspiration runs or cycles and the number of reagents utilized for each reaction chamber 44.

During execution, the test can be stopped in order to perform any necessary function or desired manual function for the superfusion device, such as clearing an obstruction or refilling aspiration vials. The automated logic of the present invention allows for pausing with resumption of test execution at the stage where execution was interrupted.

During automated test execution, the pump reagent cartridge will move to the designated starting row of the delivery to rack 34. The aspiration arm 37 will move to the designated initial row and the collection tubes 40 will be lowered into the appropriate aspiration vials of the aspiration rack 32. The timed pump and stimulator sequences will begin to pump the appropriate reagents from the appropriate vials of the aspiration rack 32 and to electrically stimulate those chambers as designated by the test parameters established. At the end of each timed pump stimulator sequence, the pump motor can be stopped and if necessary reversed to empty the tip of the collection tube 40 of the current reagent thereby preventing dripping from the collection tubes as the carriage moves to the next collection row thereby avoiding contamination of reagents. The above cycle of events repeats continuously until the last row of the test has been executed. During all of these steps, the appropriate effluents are collected in the appropriate vials of the delivery rack 34 by movement of the delivery rack underneath the delivery tubes 46 as appropriate.

Upon completion of the test, the aspiration arm will move to the position illustrated in FIG. 1 where the pick up tubes 40 are removed from all the vials and the pump/reagent carriage will move to the rear of the machine, as illustrated in FIG. 1, to facilitate the removal of the collection rack 34 and its files contained therein. The automated logic for executing the above automated testing is illustrated in the flow diagrams of FIGS. 18-24 and will be described in general terms as to the overall scheme of the logic below.

Figure 18:
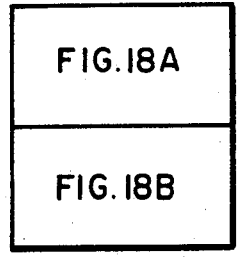
Figure 19B:
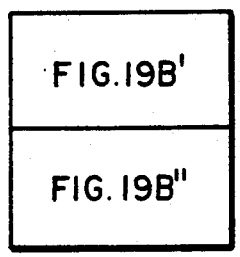

FIG. 18 illustrates the initial start up of the automation program. The system is booted and the parameters are set. The program then makes a logical check to determine if a library file has been created and if not creates a library file with zero entries. Next, the main menu is displayed and the system waits for a selection therefrom. The selection input is evaluated to determine if it is an appropriate selection and if so, the selection is evaluated to determine if it is an indication to quit the program. If the quit selection has been made, the program terminates, if not, the evaluation is made to determine if the selection was a create, a modify, a view, a delete or a run selection. The execution of each of the above selections is illustrated in FIGS. 19-24.

Figure 19A:
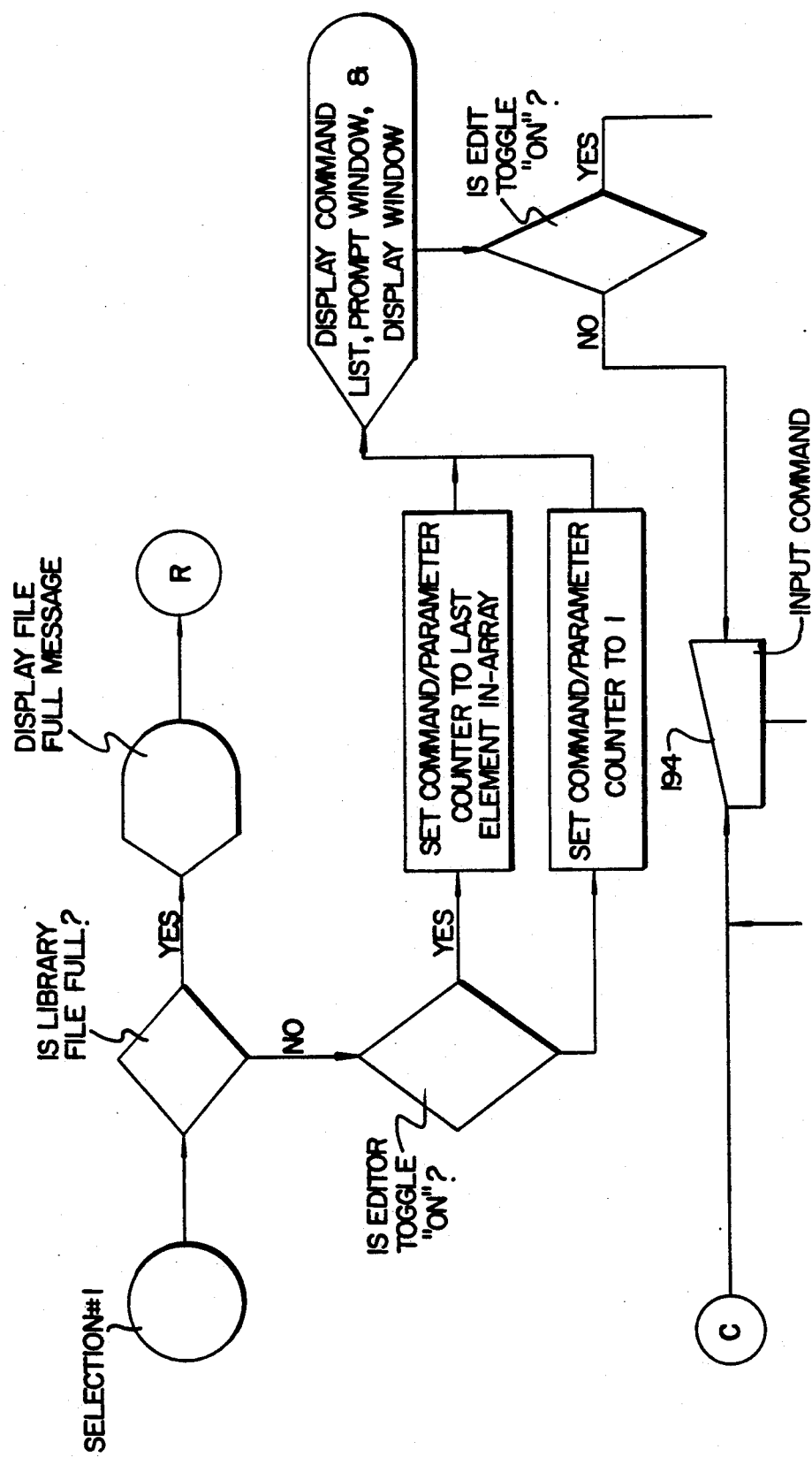
Figure 19B:
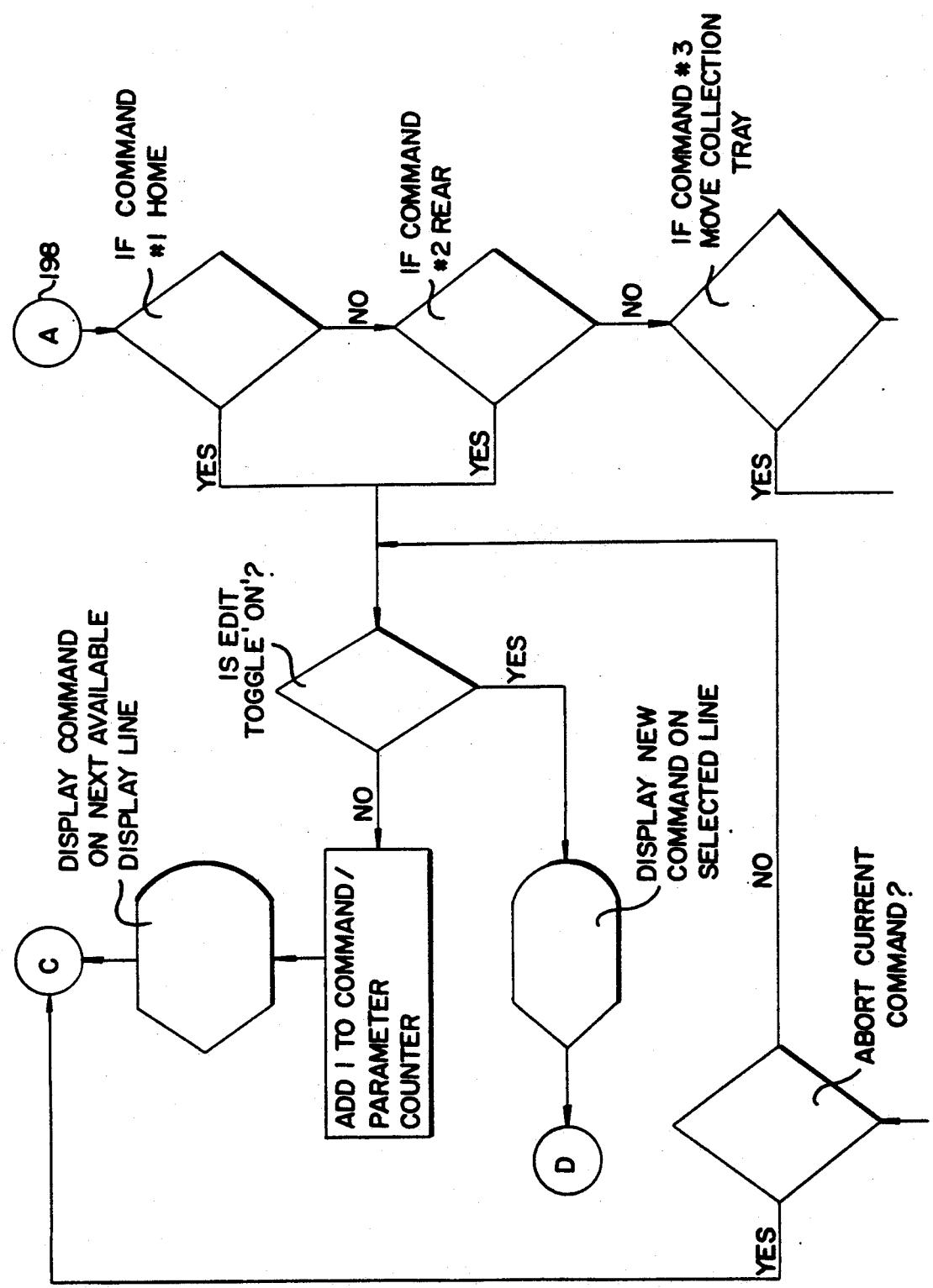
Figure 19C:
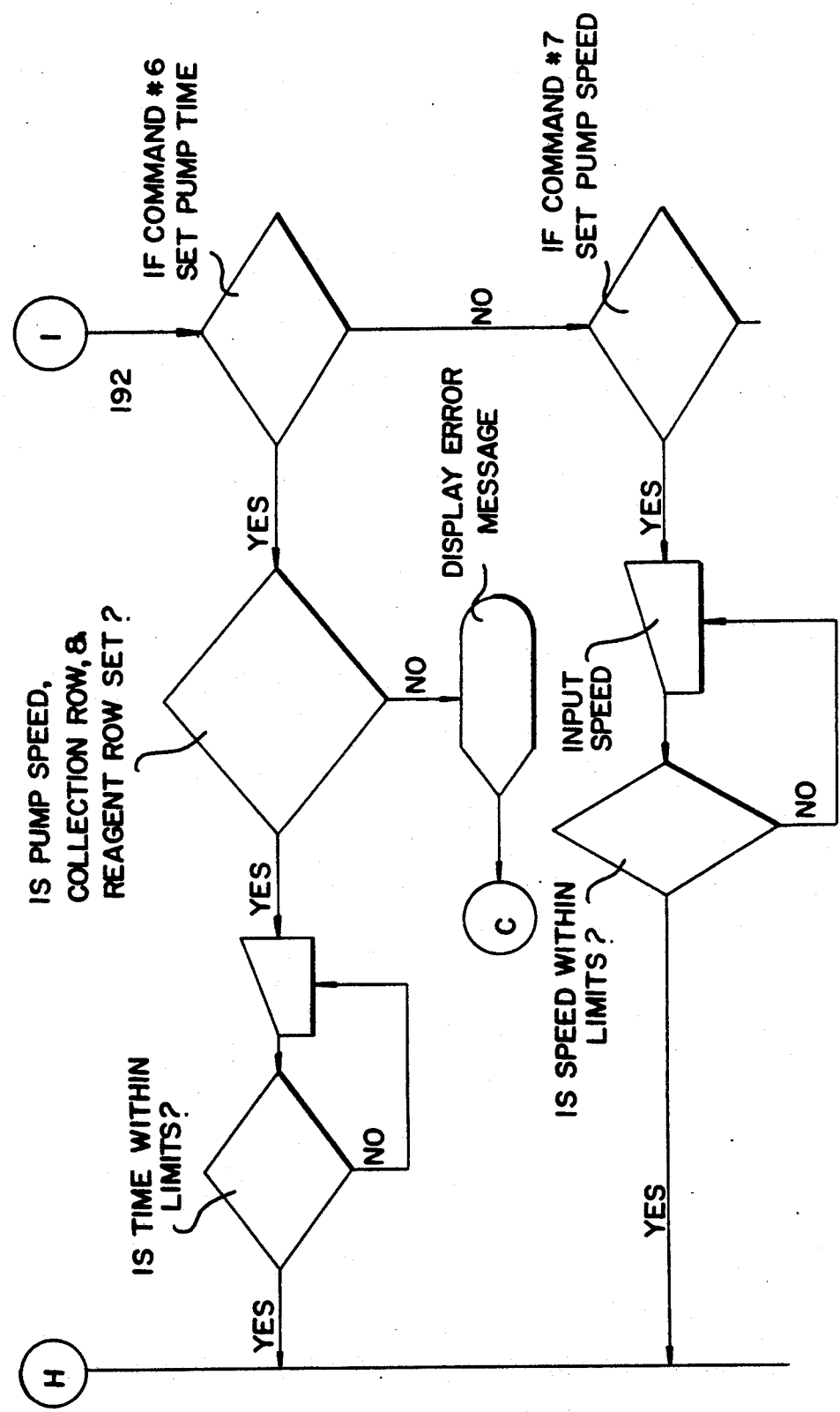
Figure 19D:
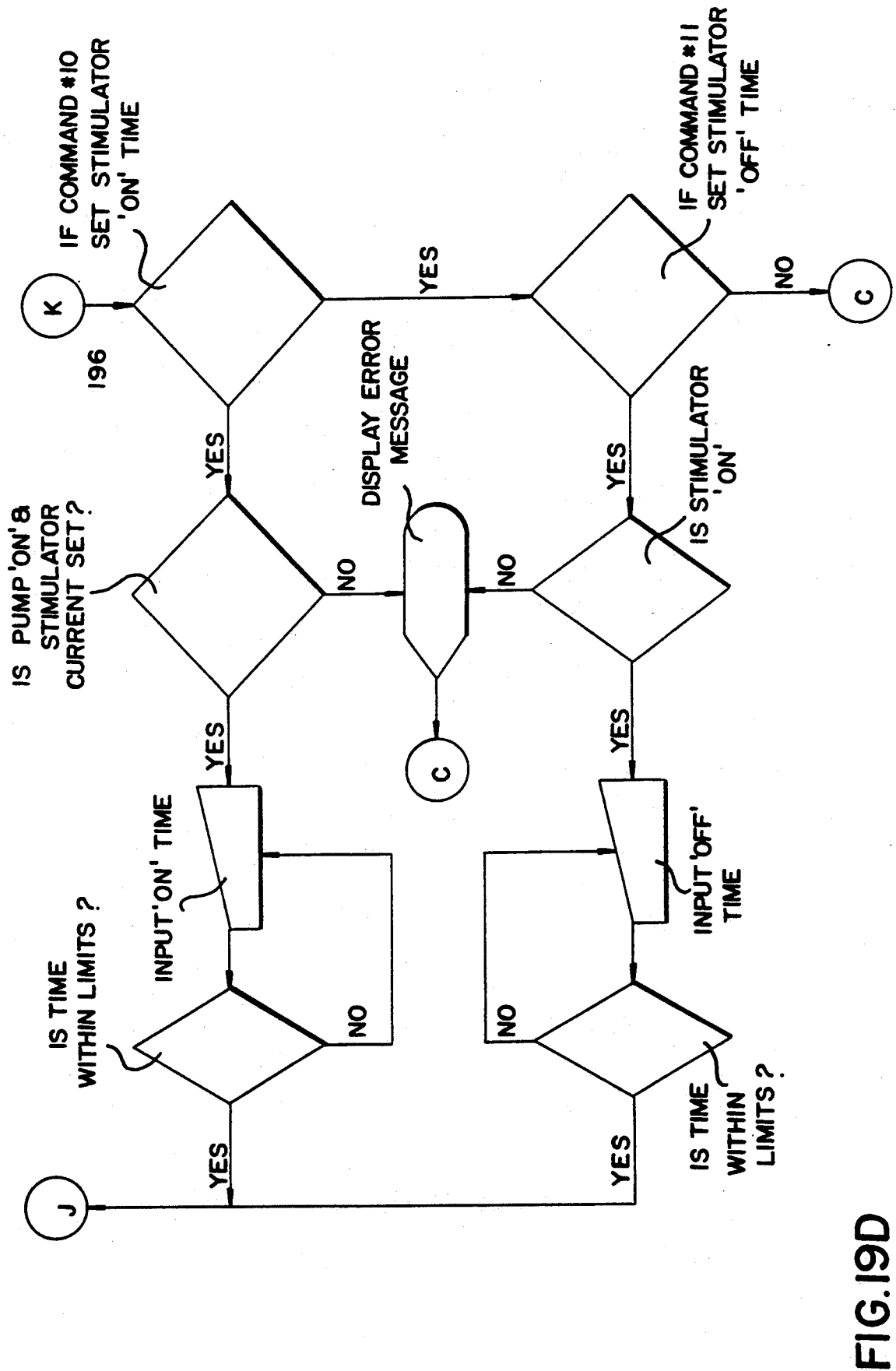
Figure 19E:
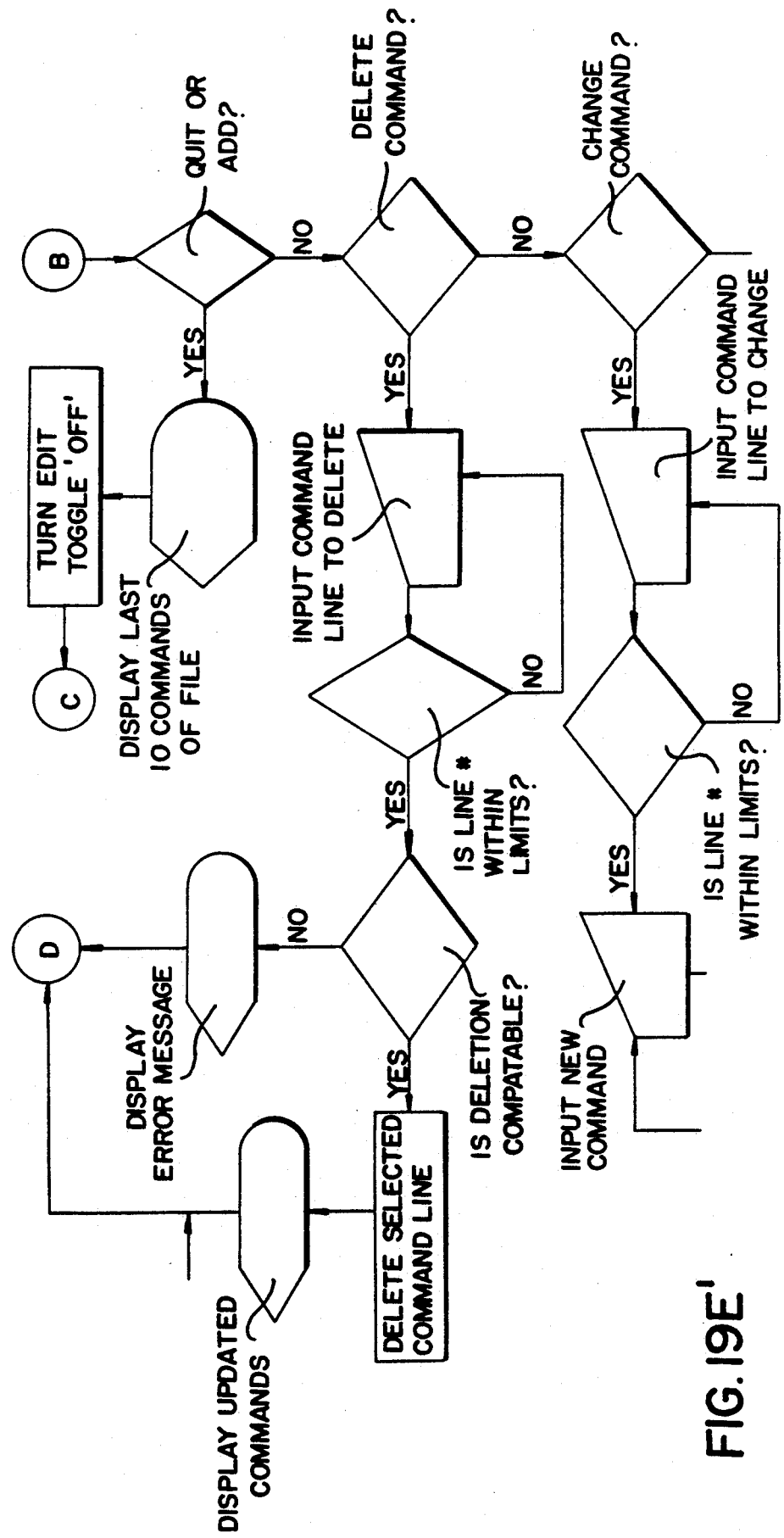
Figure 19F:
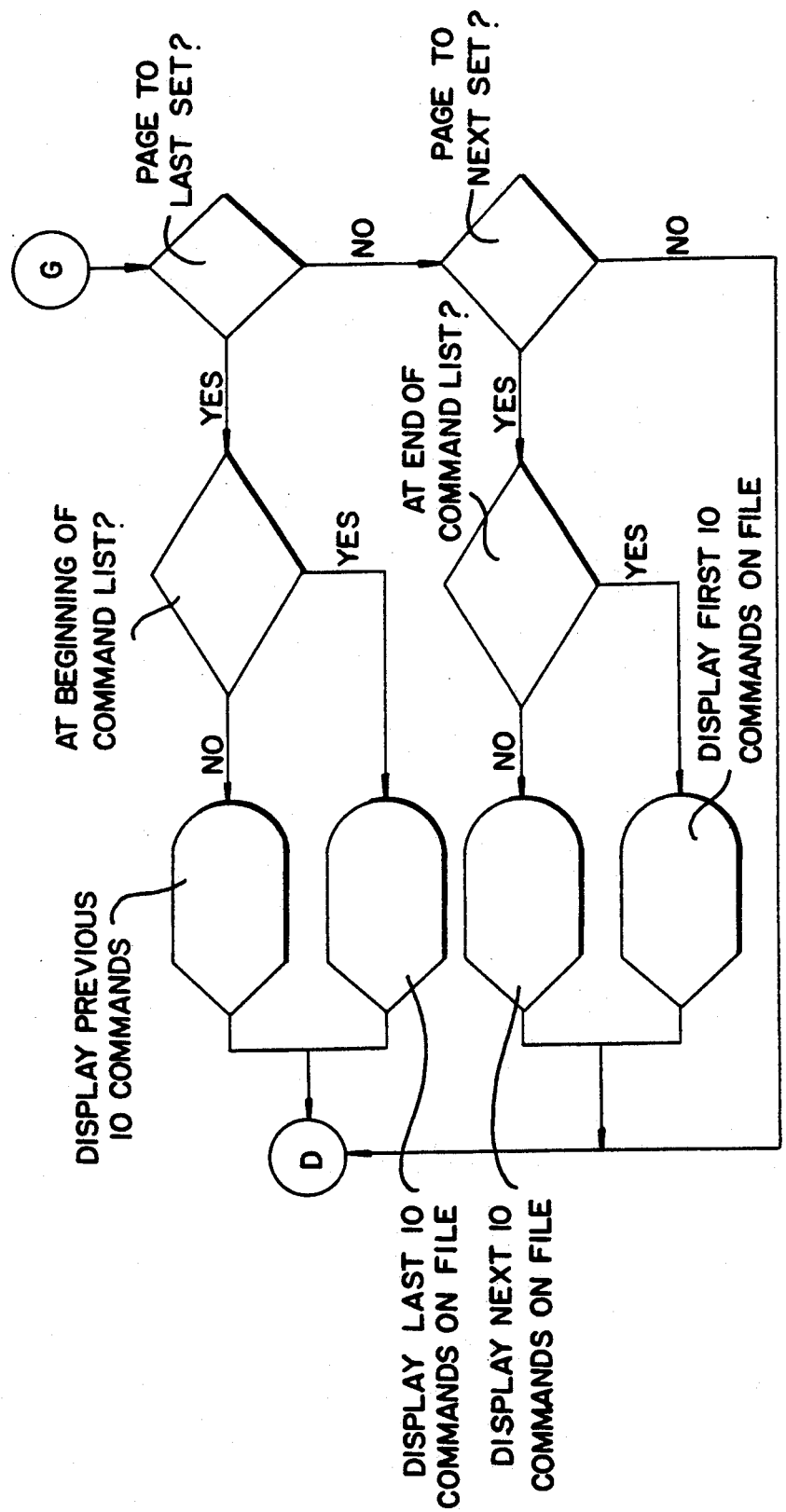

If the create and save selection has been made, flow continues into the logic operation illustrated in FIG. 19A wherein the appropriate file editors are called up to allow the automater to edit files, to provide test parameters. If the automater has selected to edit an existing file, the flow is to the logic sequence designated 195 of FIG. 19A wherein the commands to be edited are displayed and the edit inputs are evaluated. This flow continues on to FIG. 19E-stet where additional commands can be added, deleted or changed, each input being evaluated for appropriate limits and appropriate command changes. Finally, after inputs are evaluated as illustrated in FIG. 19E, it flows to FIG. 19F where the final commands of the editing are evaluated and flow is returned back to D, 197 of FIG. 19A where a decision to edit is again remade.

If the initial decision at block 193 is made to create a new test parameter file, logic flows to block 194 and continues where the automater is given the choice of inputs between 1 and 12 to select the parameter to be set. Flow is then to A 198 of FIG. 19B and continues on to I 192 of FIG. 19C which continues on to K 196 of FIG. 19D. Each of the initial boxes #1-#12 in this logic sequence evaluate the selected input. Flow is then directed to the appropriate logic set for entering the parameters selected, such as collection tray movement, reagent probe movement, purge time, pump time, pump speed, gas time or stimulator current. When all desired parameters have been established as described above, the test parameters are named and saved.

Figure 20:
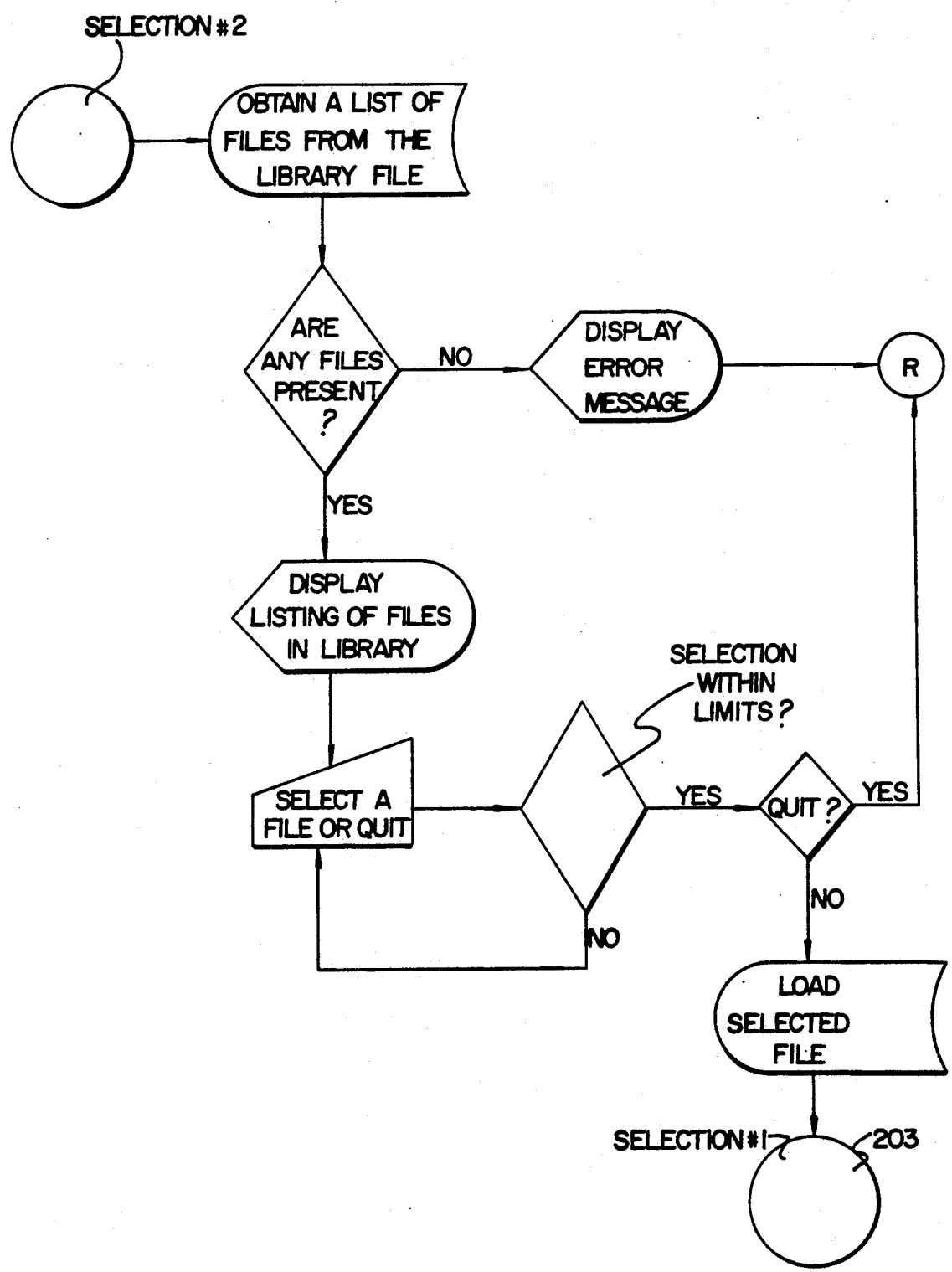
Figure 21A:
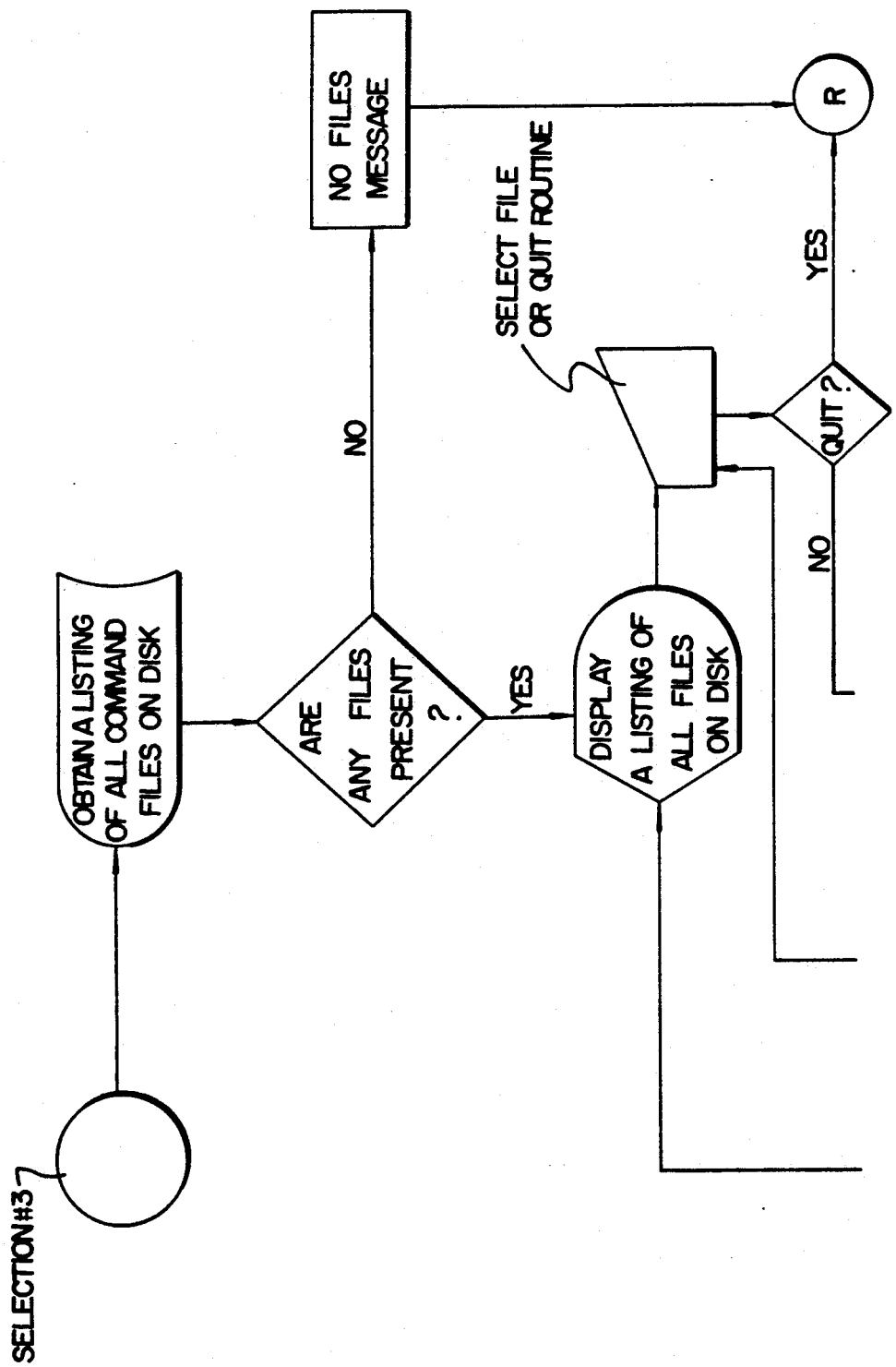
Figure 21B:
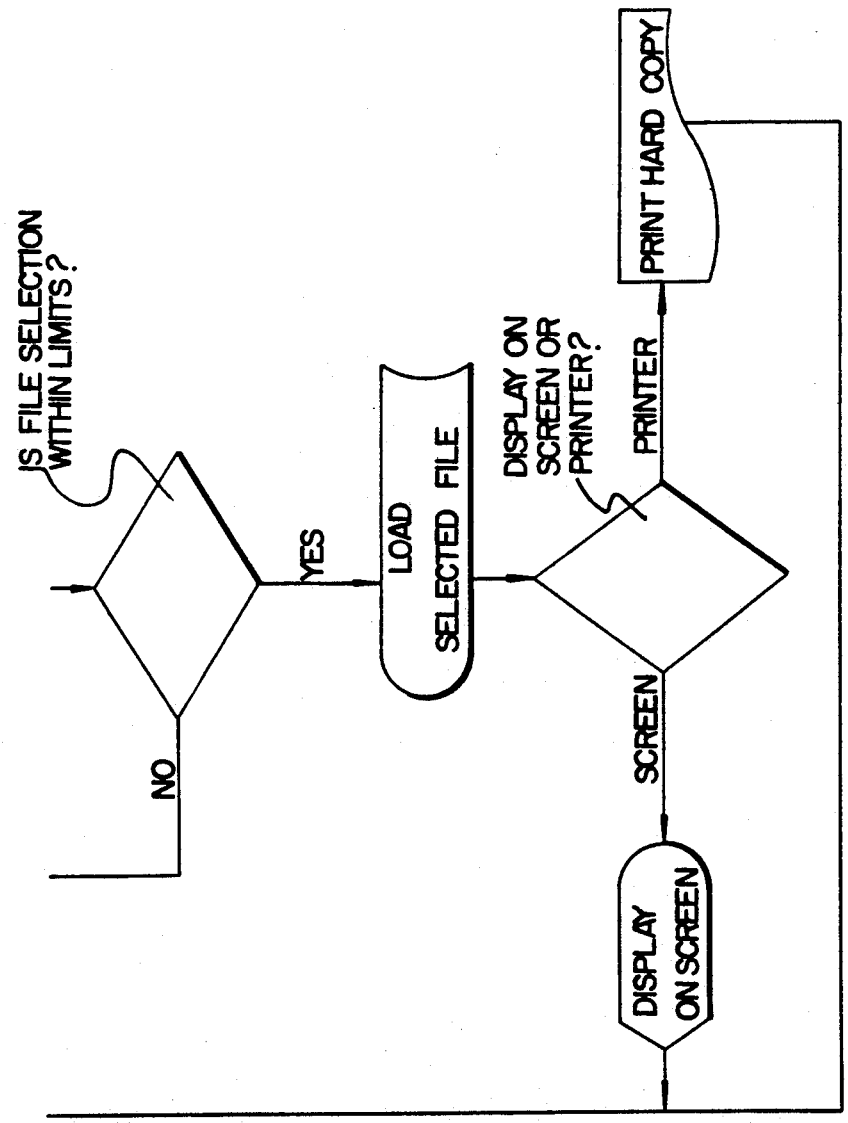
Figure 22B:
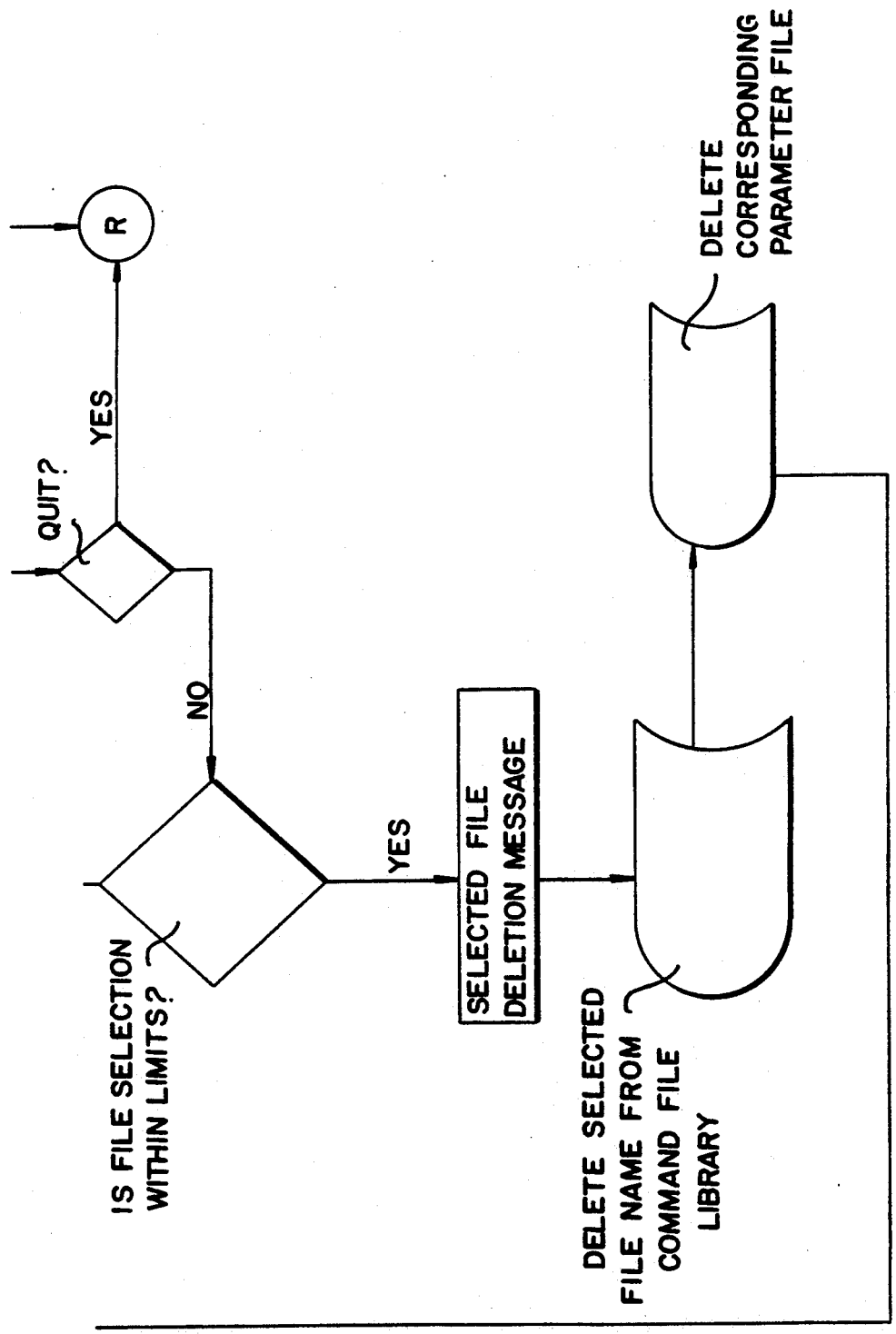
Figure 23A:
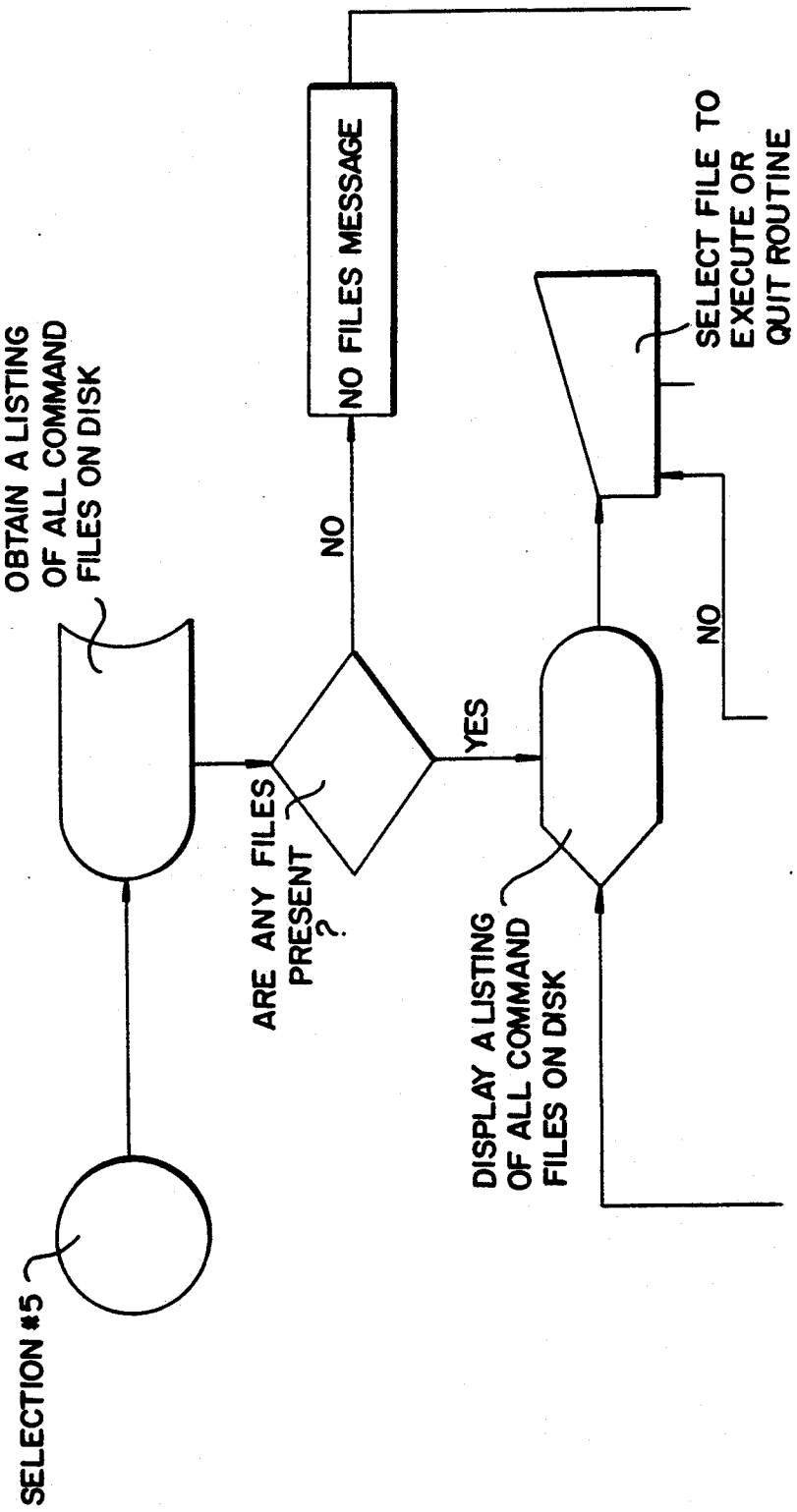
Figure 23B:
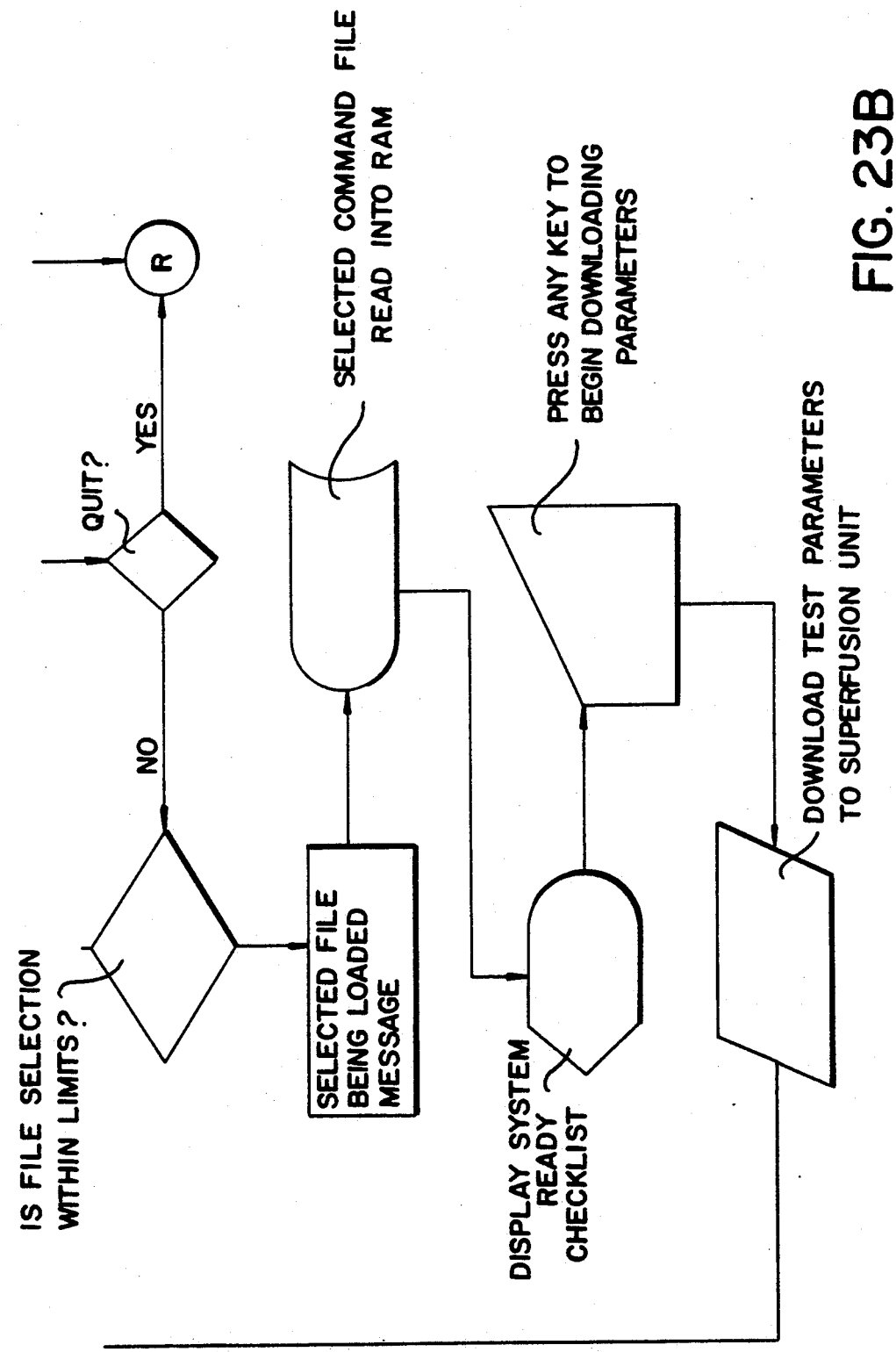
Figure 24A:
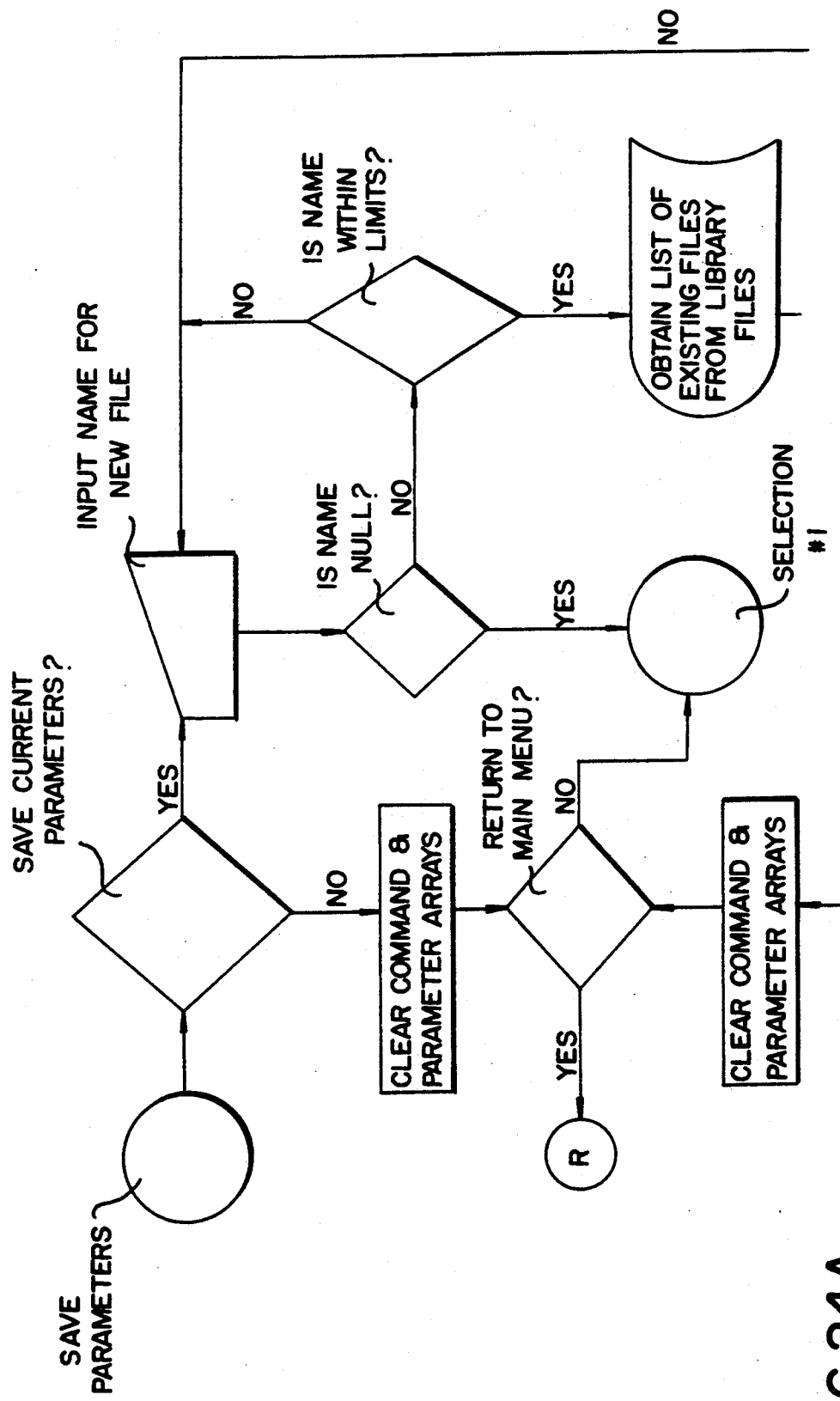
Figure 24B:
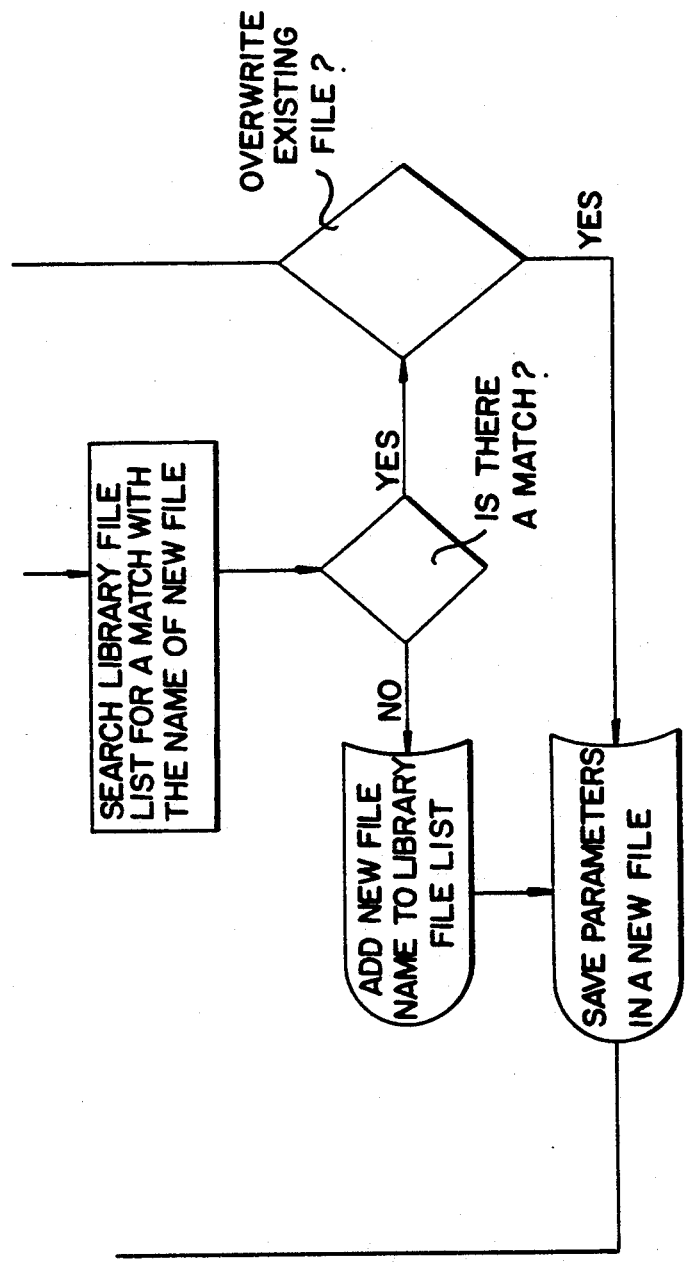

FIG. 20 illustrates the logic sequence for modifying a set of commands in a saved set of test parameters. Logically, a list is obtained of all of the saved tests and a selection from the list is allowed. Once the selection is made, the selected file is loaded and flow then is branched to the create and save logic sequence at block 203 and directed to the flow illustrated in FIGS. 19A through F.

Figure 21:
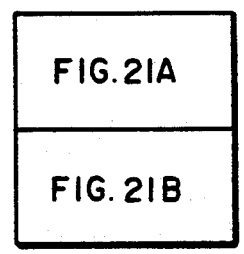
Figure 9B:
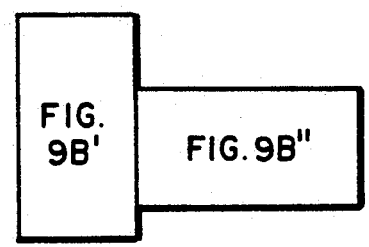

FIG. 21 illustrates the logical flow for viewing or printing a set of test parameters from a selected saved test. Logically, the tests are brought up, the operator is allowed to make a selection. A selection is validated and the appropriate file loaded. Once loaded, the operator selects to display the test parameters on a screen or to print a copy thereof.

Figure 22:
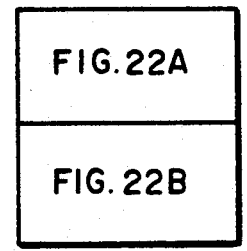

FIG. 22 illustrates the logical flow for deleting a saved test. Again, the list of saved tests is brought up, validated and a selection is made. The selected file is then accessed and its deletion is indicated by the operator. The selected test file is deleted.

Figure 23:
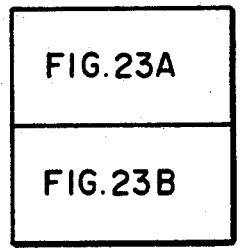
Figure 19C:
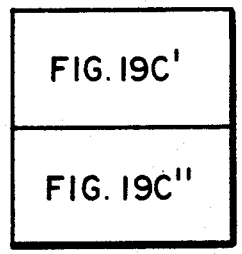

FIG. 23 illustrates the logical flow for initiating the execution of a saved test and execution of the test parameters contained therein. Again, the list of saved tests is brought up and the operator selects therefrom. The selected test file is then loaded and the check list detailed above is prompted to the operator to assure that the automated superfusion device is properly set-up before initiation and execution of the test. The test parameters corresponding to the selected tests are then downloaded through the communication cable 96 illustrated in FIG. 8 to the automated superfusion device. The automated superfusion device receives, stores and executes these parameters and instructions as described below.

Figure 24:
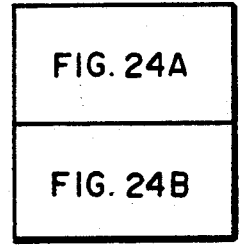
Figure 19E:
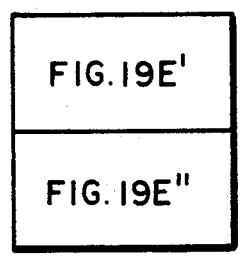
Figure 9A:
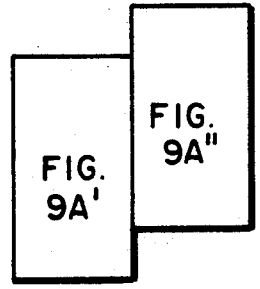

FIG. 24 illustrates the saved sequence undertaken when the save parameter selection has been made from the logical flow illustrated in FIGS. 19A box 199. The current established parameters are saved to a test file which is identified by a new test file name. The name is checked for overlap and then read into the list of files if no overlap exists. Otherwise an alternative name must be chosen.

The blocks R of FIG. 24 which corresponds to the R blocks of the preceding FIGS. 19-23 indicates a return to the main menu block R of FIG. 18. Each of the above described routines returns back to the main menu portion of FIG. 18 from which the program can be quit as earlier described.

Figure 9A:
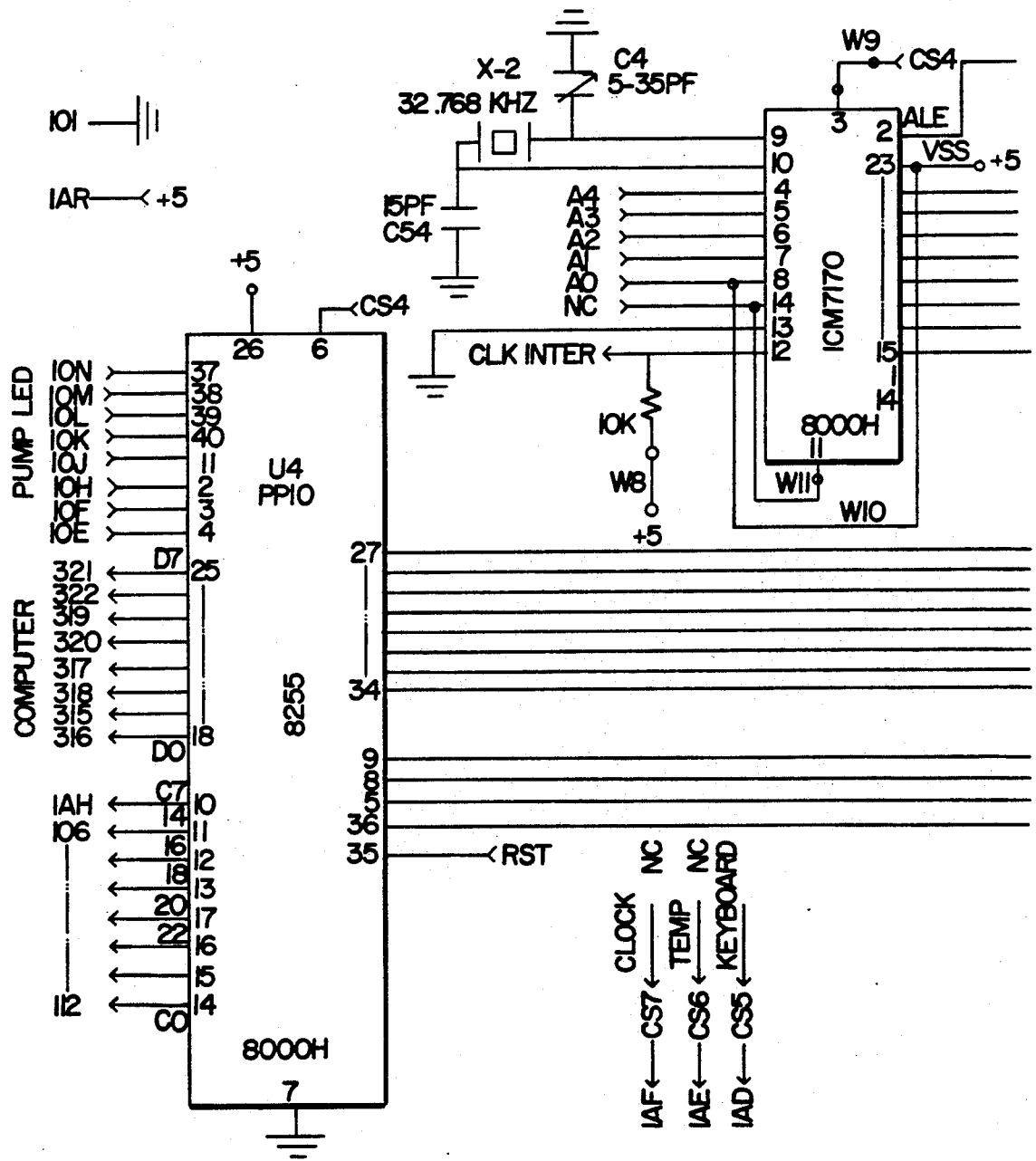
FIG. 9A and 9B is a schematic wiring diagram illustrating the microprocessor board for controlling the superfusion device.

Once the desired test sequence has been established through the software, the test sequence is then sent to be superfusion device 30 for execution. As illustrated in FIG. 8, the computer 90 and the superfusion device 30 are tied together by a communications cable 96. The necessary data for execution of the desired test sequence is fed into U2 as illustrated in FIG. 9A along input lines 98. The instructions are processed and passed along to processors U3, U4, U5, U7 and U1.

Processor U3 controls the display from the superfusion device to indicate the testing sequencing. Processor U1 is utilized to control the positioning of the collection tube rack 34 while U2 controls the positioning of the reagent tube rack 32 and pick up tube arm 37. The pump control and feedback to the computer is processed in U4. U5 is the main controller for the system which executes appropriate timing between and among the above functions and interprets the test instruction set to coordinate the pumps reagent and collection apparatus.

Figure 10:
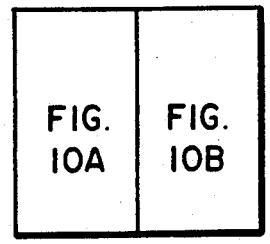

FIG. 10 illustrates in greater detail the actual controllers for the horizontal positioning of the reagent rack 3 and the collection rack 34. As well as the controller U4 for actuating the appropriate pump from the pump bank 42 so that the appropriate reaction chamber will be fed for an appropriate amount of time during the testing sequences described above.

Figure 9B:
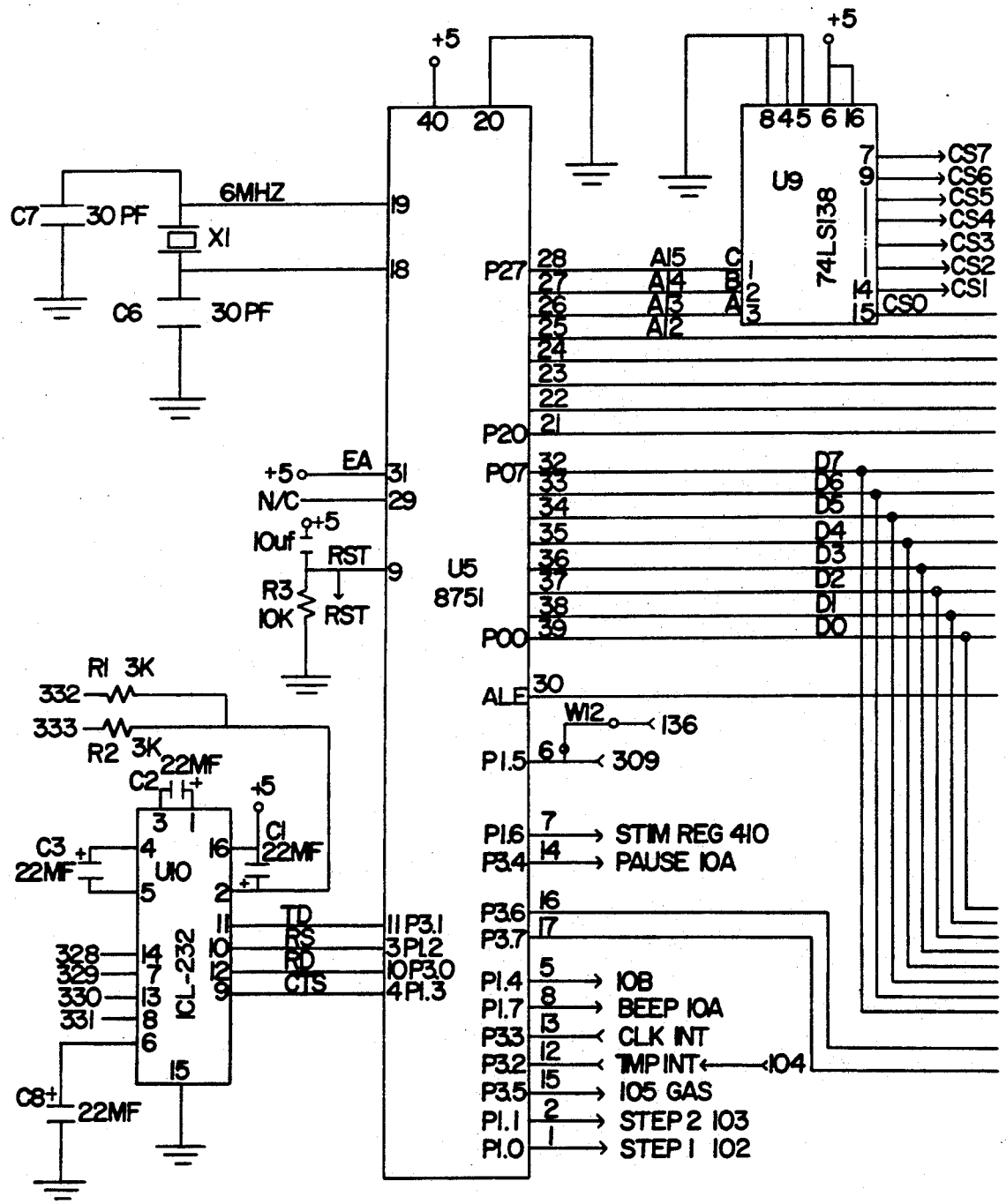
Figure 10A:
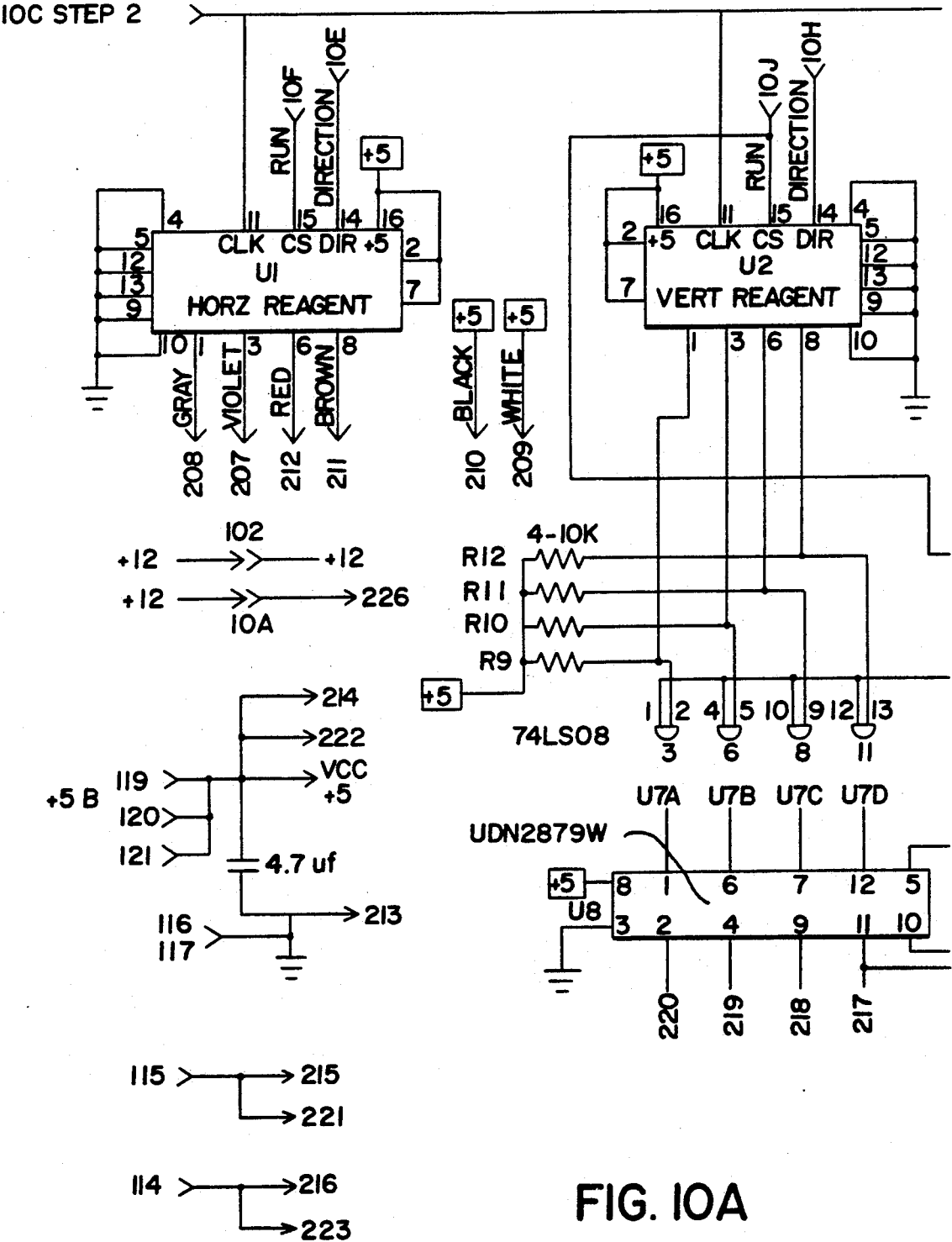
FIG. 10 is a schematic wiring diagram illustrating the timing and control circuitry for the reagent and collection processes.
Figure 10B:
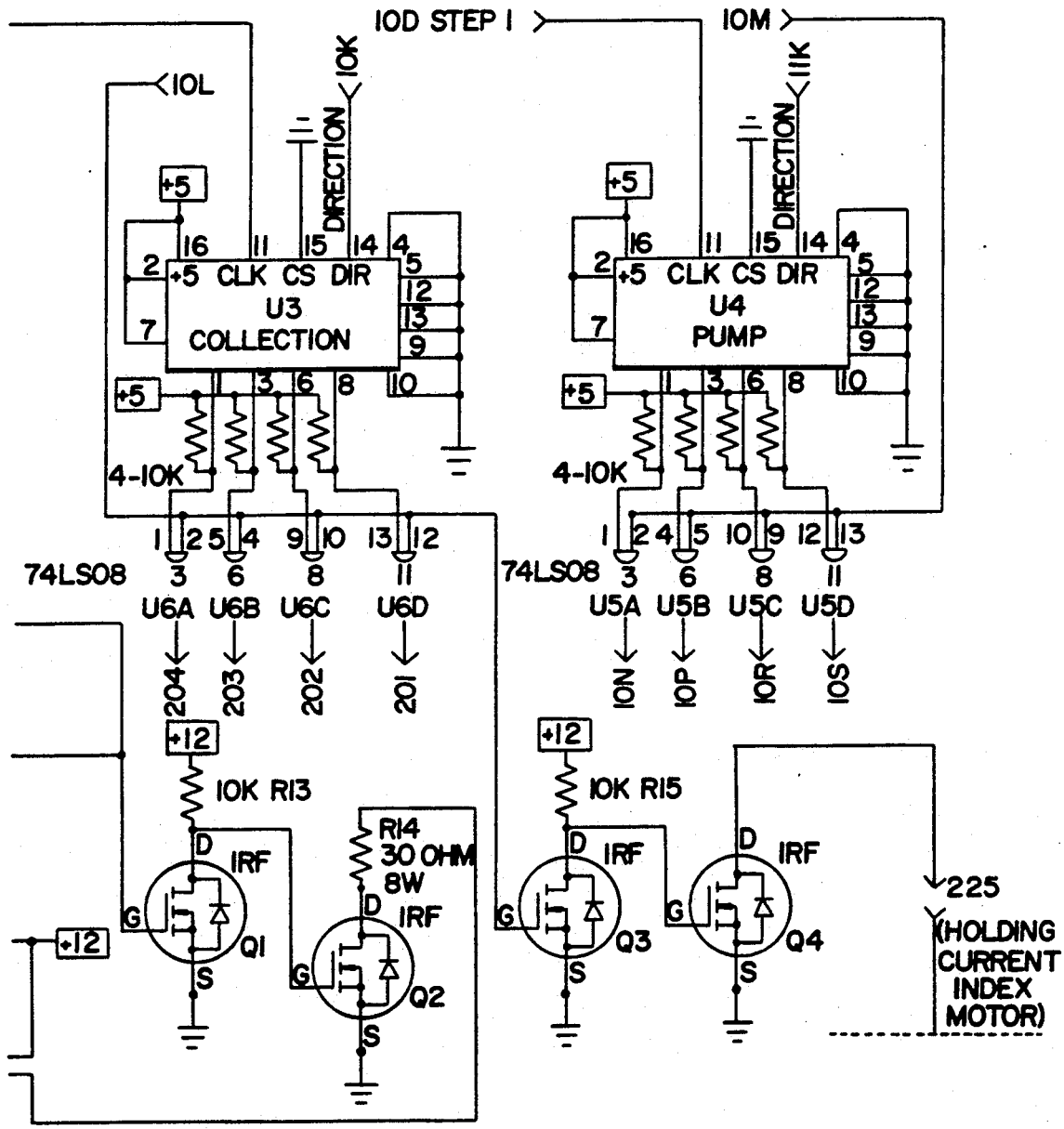
Figure 11A:
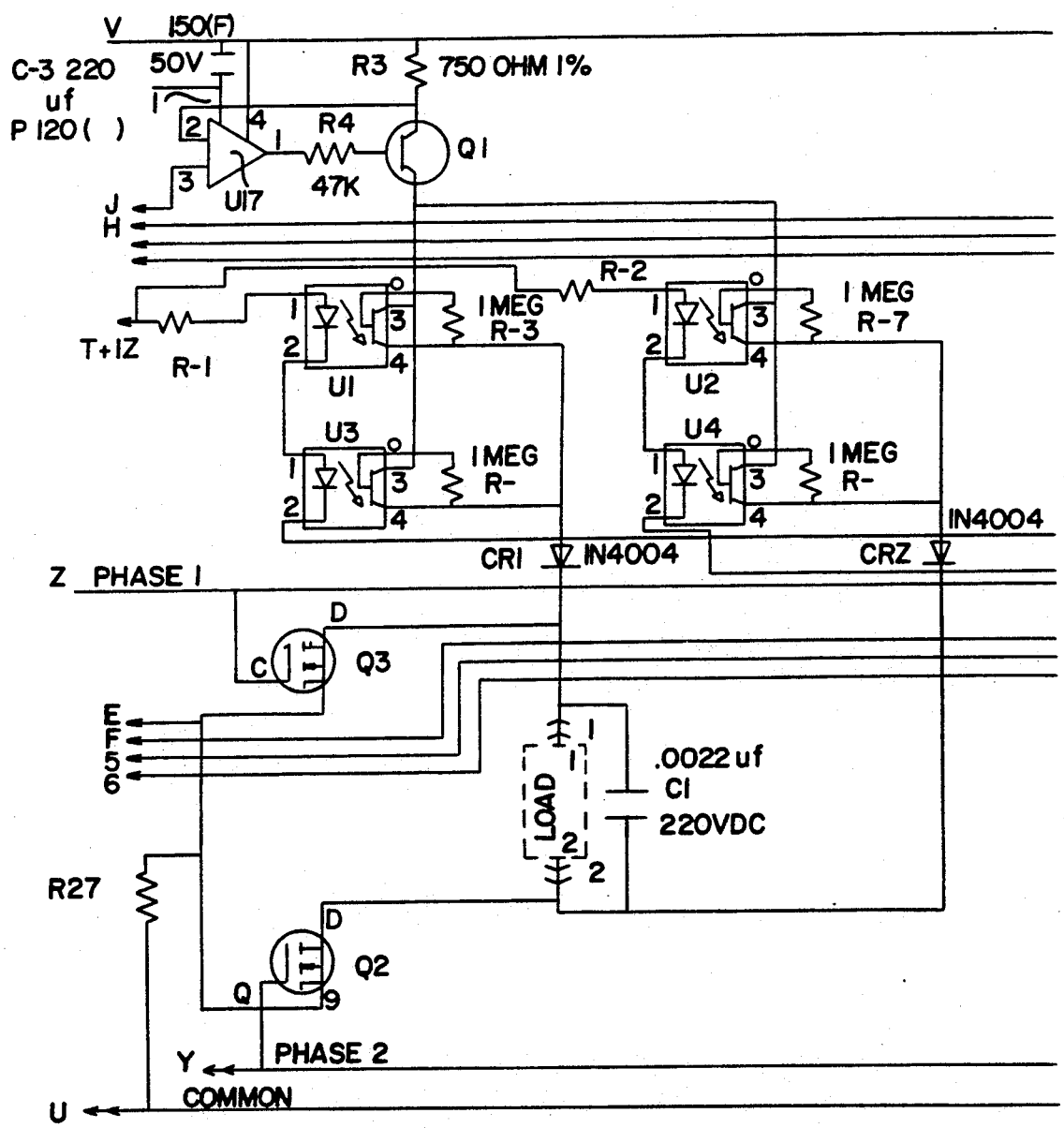
FIG. 11 is a schematic diagram illustrating the stimulator quad channel board.
Figure 11B:
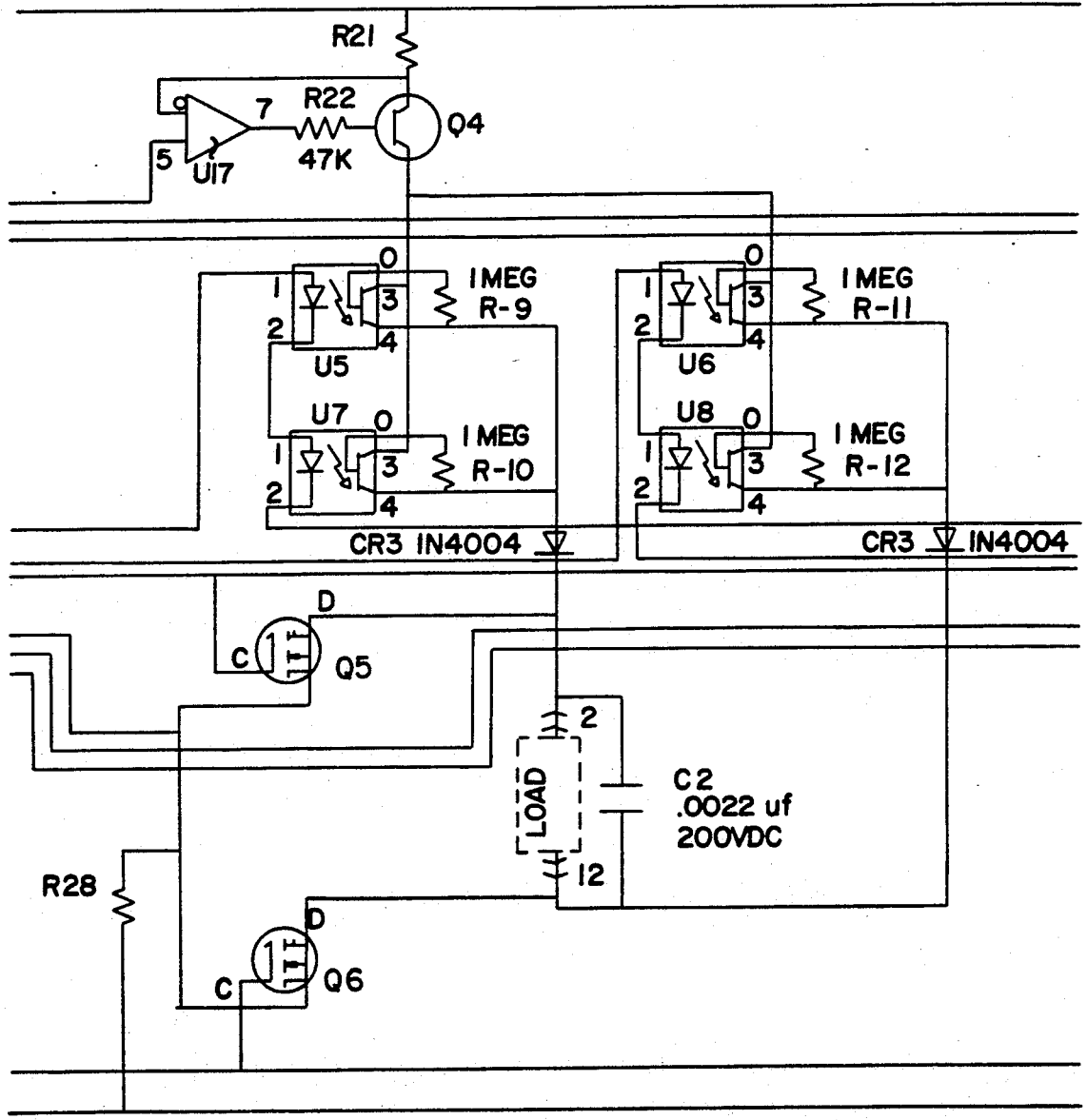
Figure 11D:
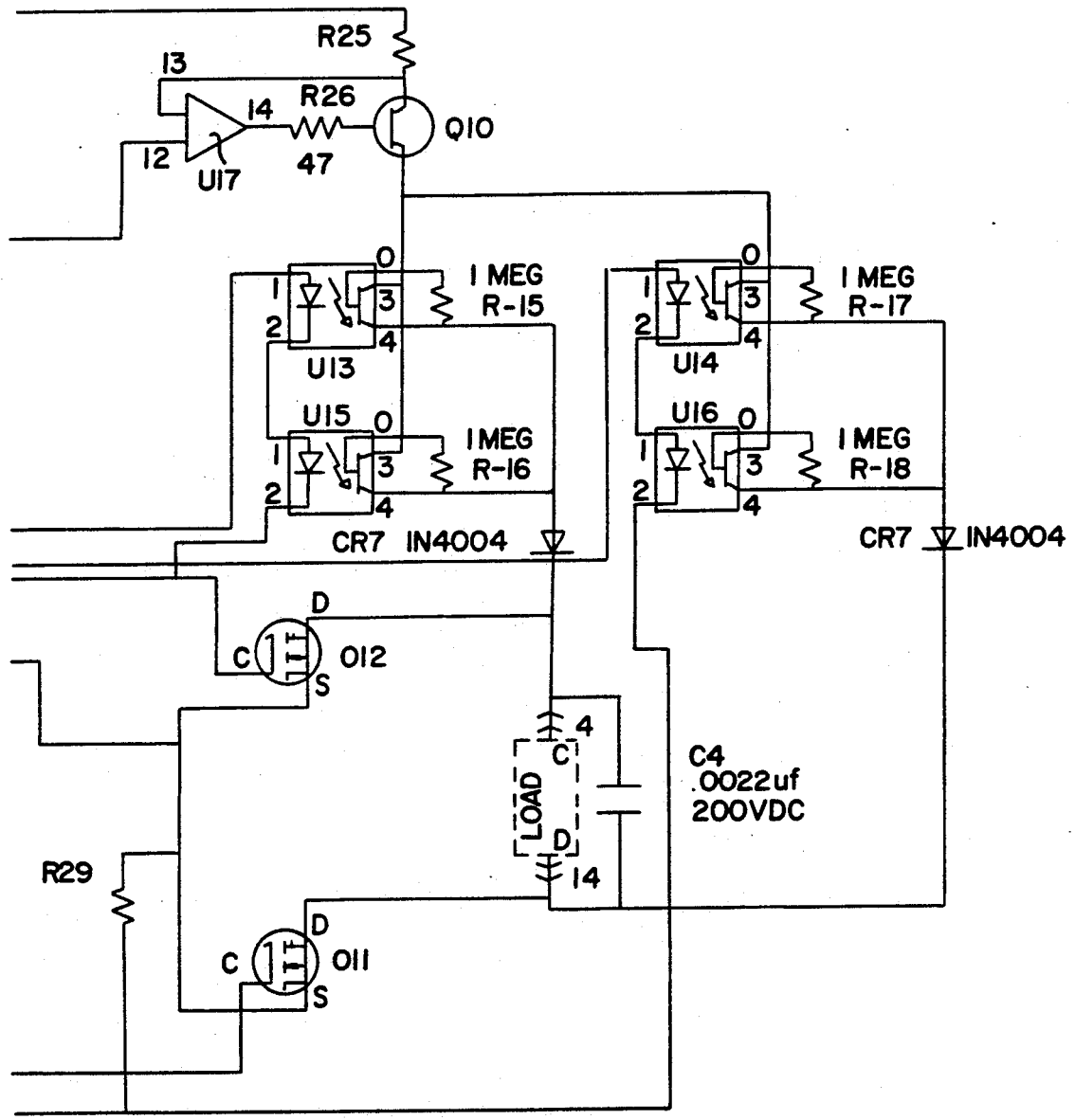
Figure 12A:
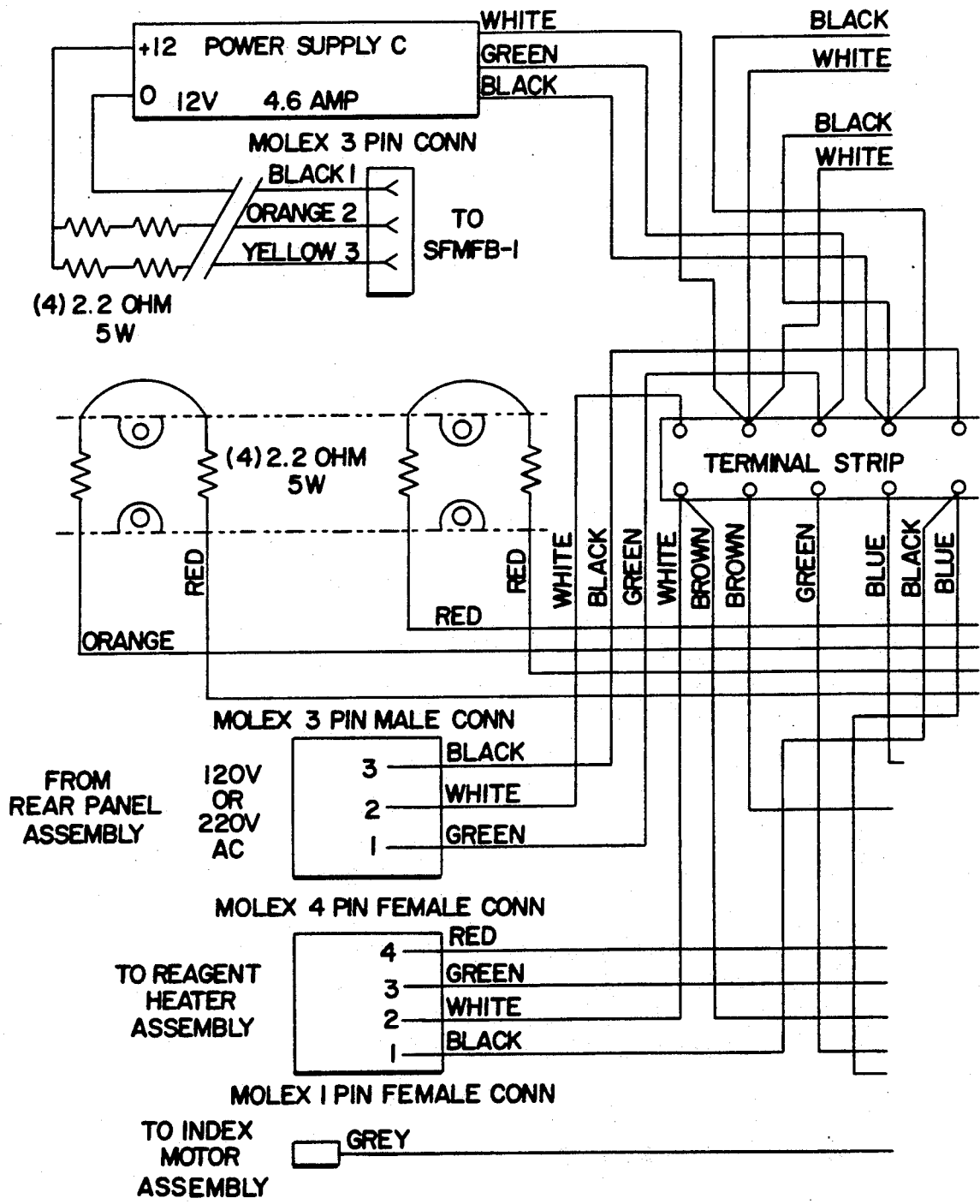
FIG. 12 is a schematic diagram illustrating the power supply for the superfusion device.
Figure 12B:
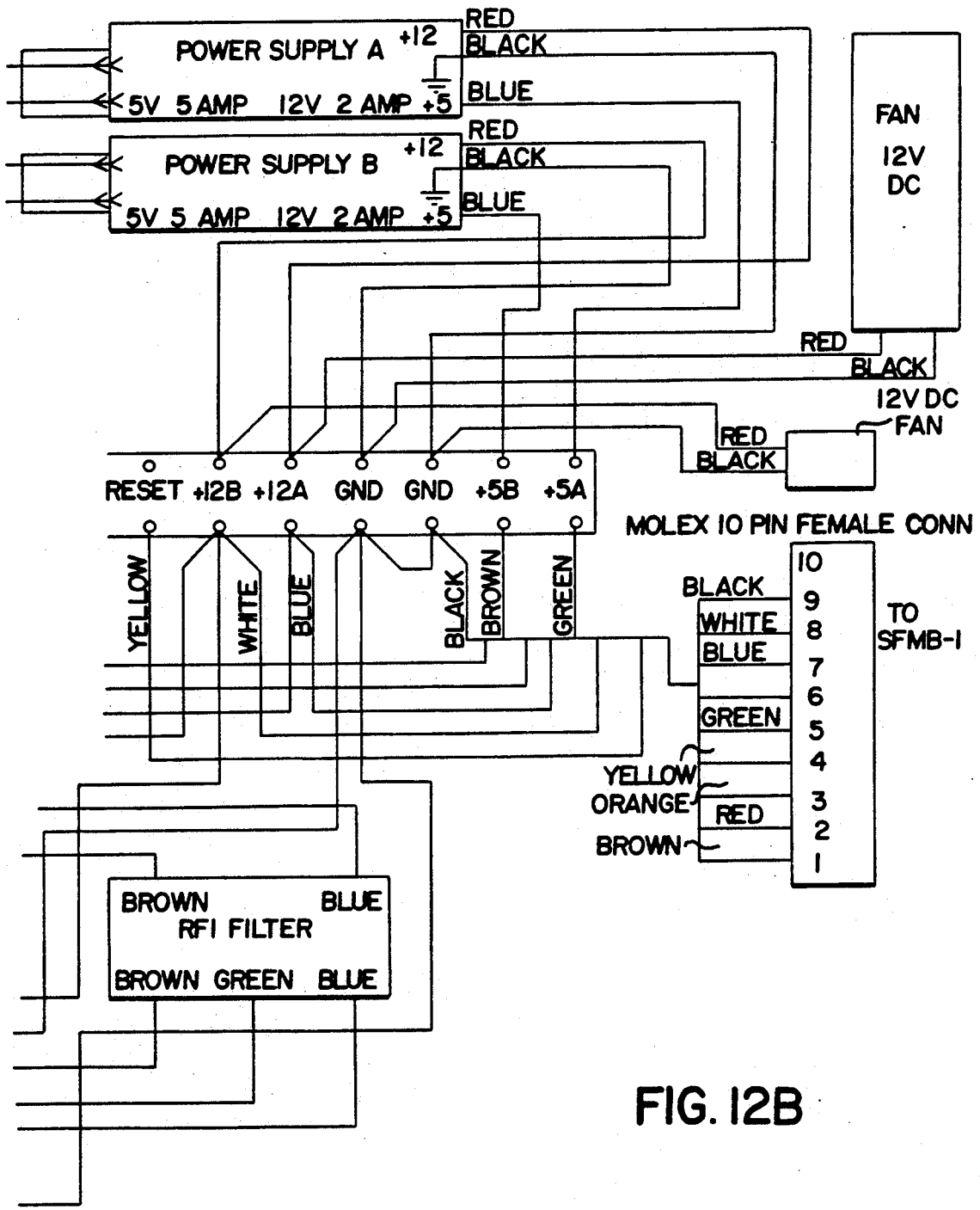
Figure 11:
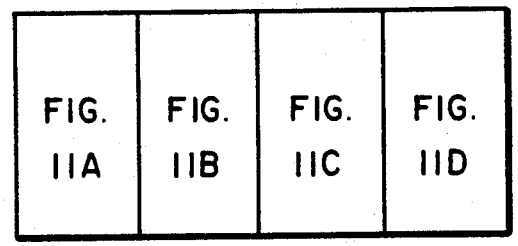

FIG. 11 illustrates the stimulator quad channel which is utilized to send the appropriate electrical stimulation signal to the appropriate reaction chamber at the specified time in the cycle and for the prescribed amount of time to provide the appropriate electrical stimulation. This stimulator quad panel board receives its instructions from the master controller U5 of FIG. 9B in order to coordinate electrical stimulation with the other parameters of the specified tests. The stimulator board illustrated in FIG. 11 includes a number of semiconductor controllers in order to provide the ability to establish a desired electric potential across any of the specified reaction chambers.

Figure 12:
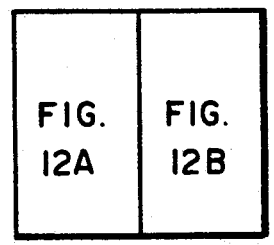
Figure 19A:
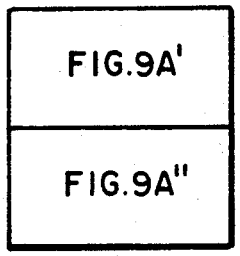

FIG. 12 is a simplified block diagram illustrating the power distribution within the superfusion device which assures that the pumps and mechanical actuating mechanisms receive appropriate power to properly position the various reactant and collection racks where appropriate and to provide a proper filtered power source for the electrical stimulation. Through the use of RF filters, the appropriate AC signal can be provided to each of the reaction chambers. While providing an appropriate AC signal of a desired frequency, polarization of the samples within the reaction chambers can be avoided through the use of bi-phase stimulation. By switching the current in one direction and in the opposite direction an equal stimulation of all samples can be obtained which prevents unwanted polarization.

Figure 13:
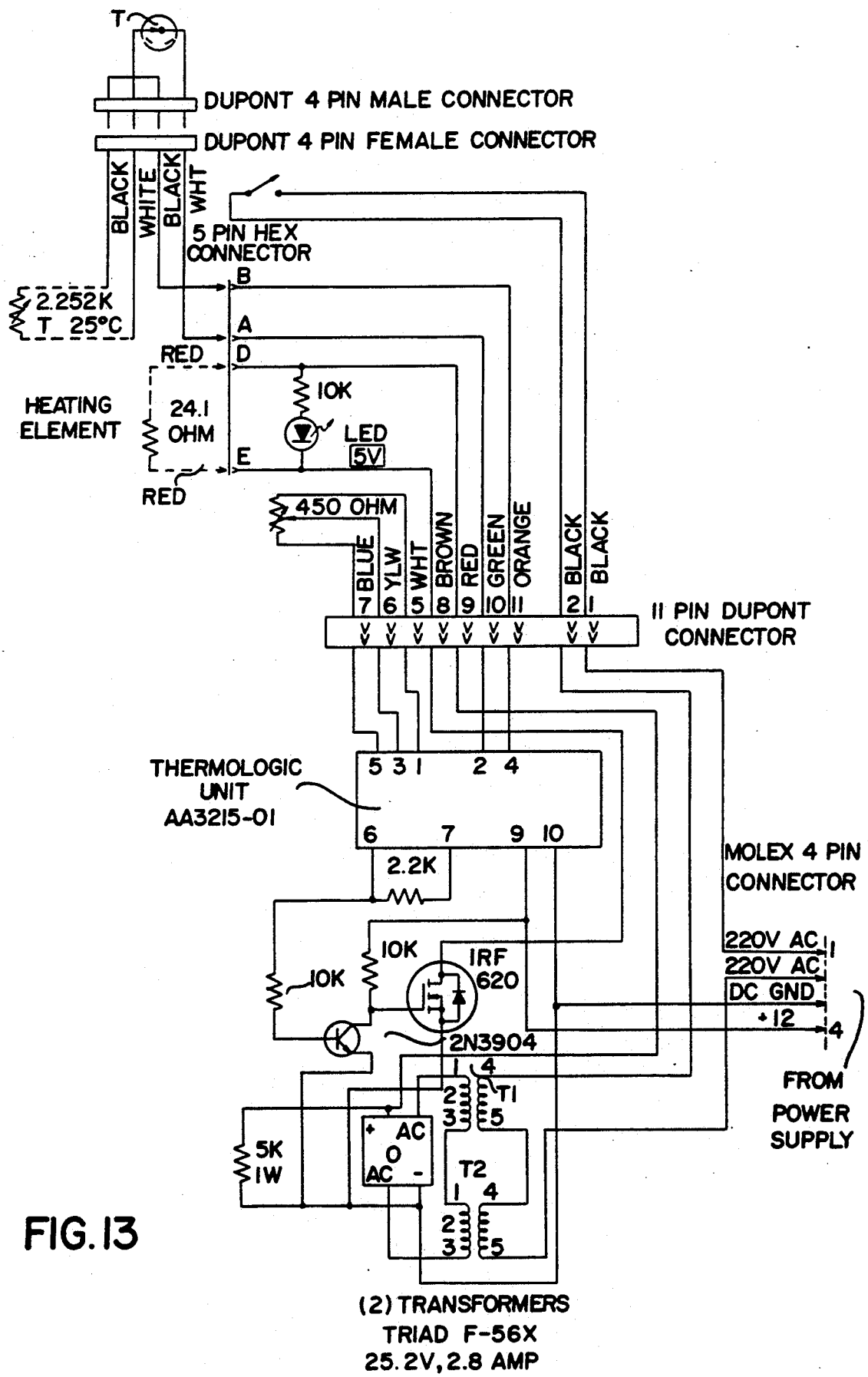
FIG. 13 is a schematic diagram illustrating the reagent bath heater circuit.

FIG. 13 provides an illustration of an exemplary reagent bath heater circuit. This circuit is utilized to maintain a constant temperature in the fluid bath 82 surrounding the reaction chambers so that the reactions may be carried out at any specified desired temperature. The thermal unit illustrated in FIG. 13 also receives its instructions from the micro controllers illustrated in FIGS. 9A and 9B to provide appropriate temperature control in proper sequencing with the operation of the test parameters.

Figure 14:
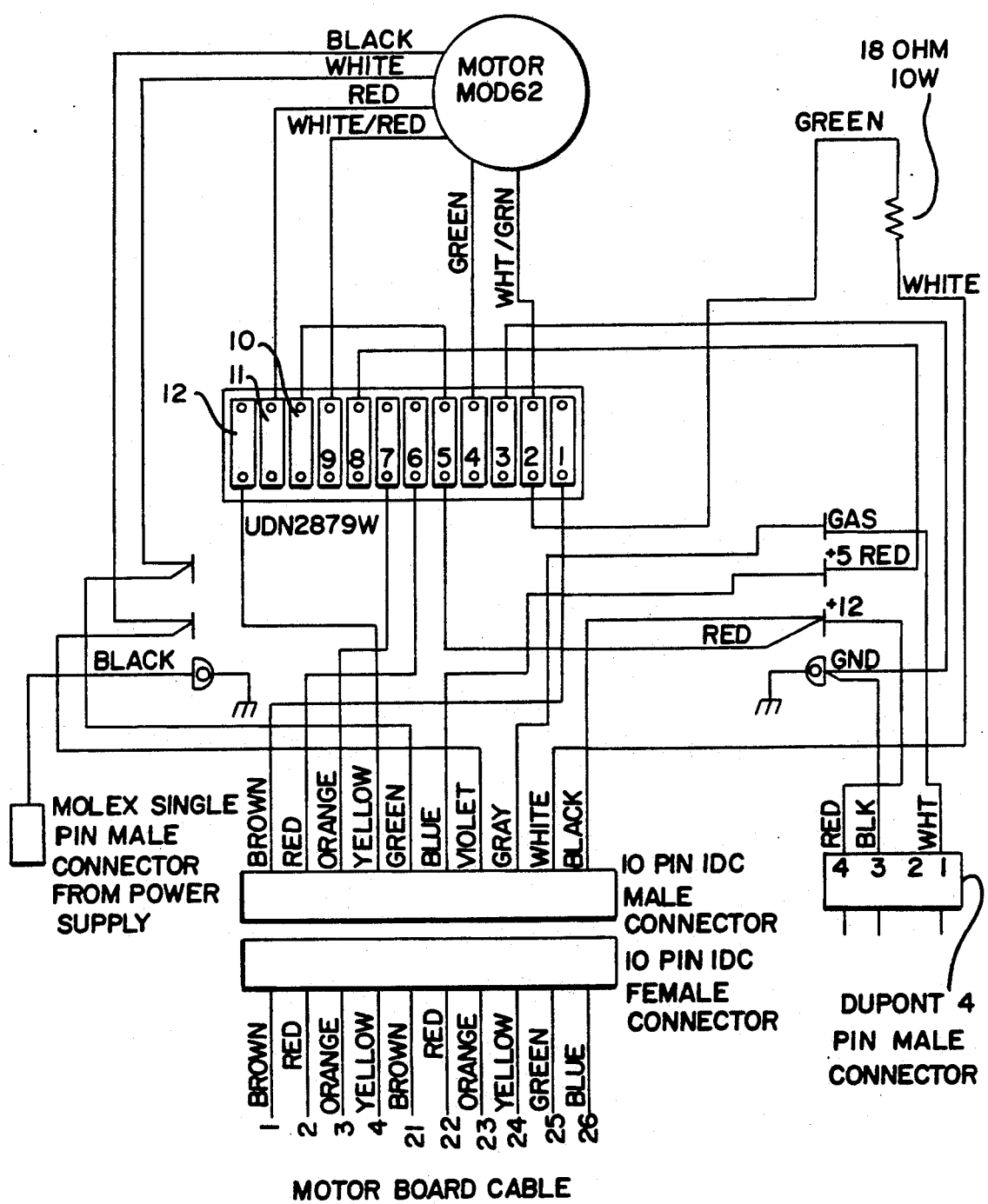
FIGS. 14 and 15 ar schematic wiring diagrams illustrating the horizontal and vertical motor drive assemblies, respectively.
Figure 15:
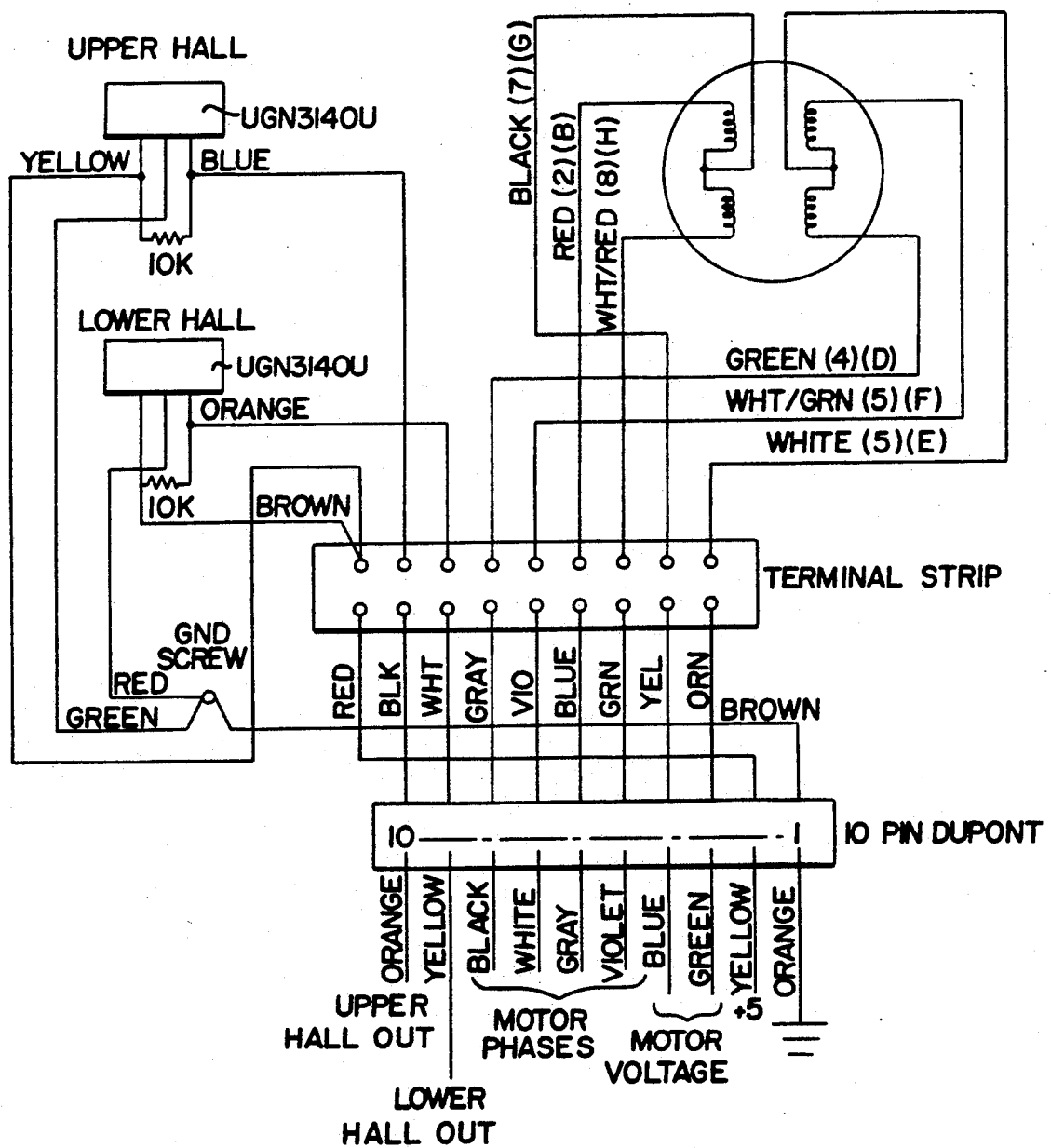
Figure 16A:
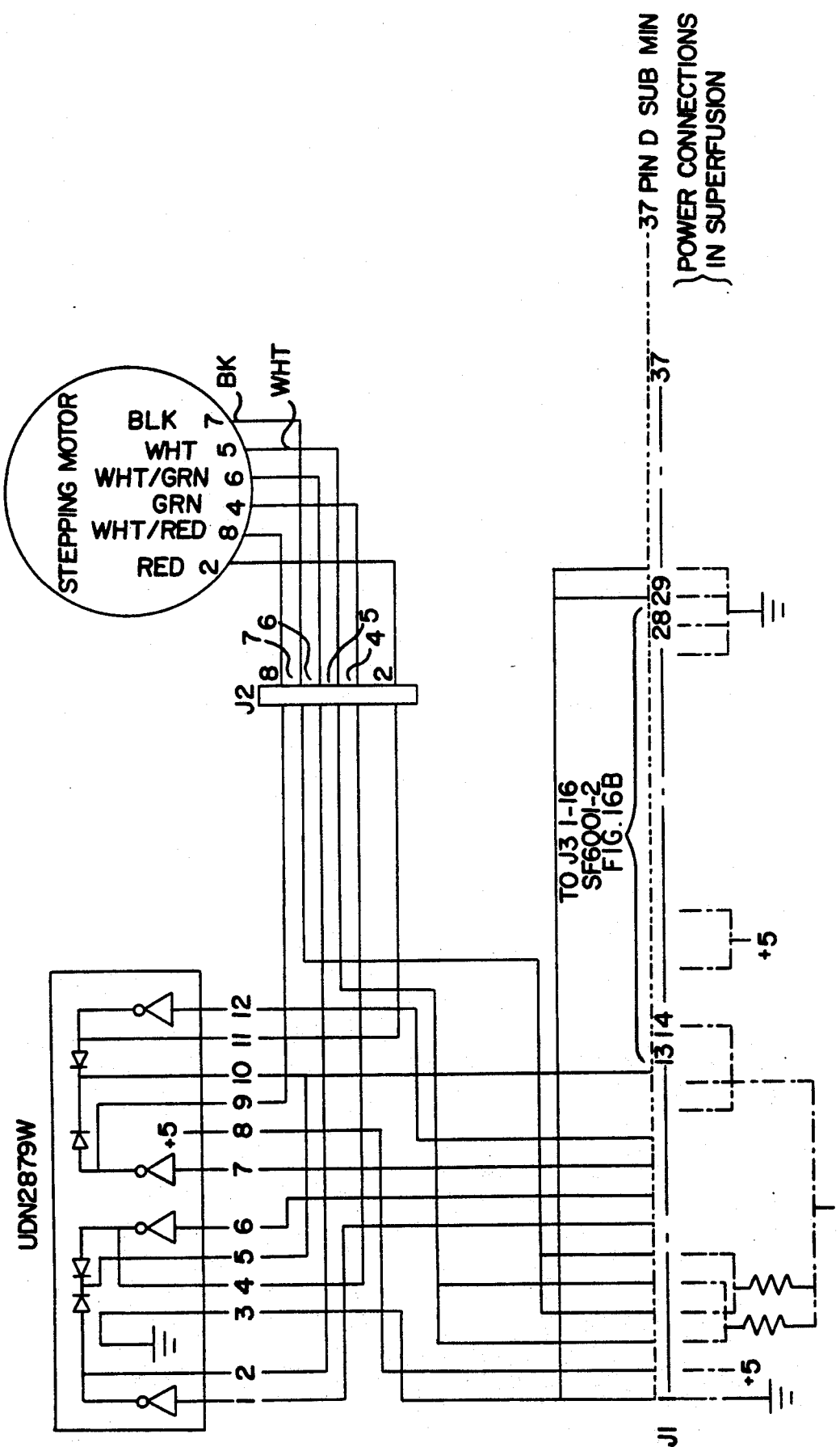
FIG. 16 is a schematic wiring diagram illustrating the control operation for the peristaltic pump.
Figure 16B:
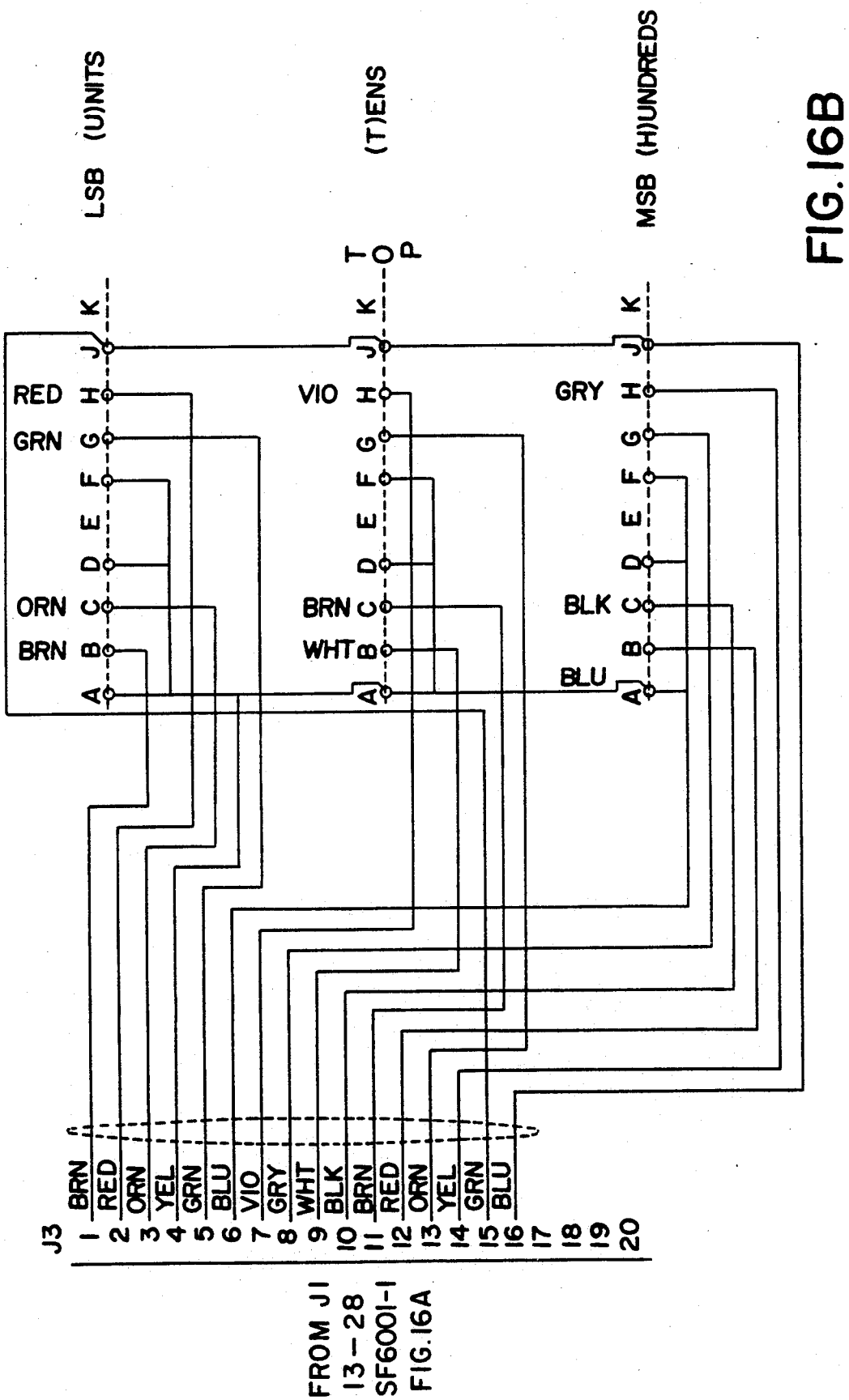

FIGS. 14 and 15 illustrate the horizontal and vertical wiring diagrams for the horizontal and vertical motor assemblies, respectively. The motors are also controlled by the microprocessors illustrated in FIGS. 9A and 9B to properly position the racks 32 and 34 where necessary with the test execution. The circuitry illustrated allows appropriate stepper motor control to precisely position the racks and tubes for accurate reagent supply and effluent collection. It is essential that the motors be equipped with the feedback circuitry illustrated so that there exact position can be determined.

Figure 16:
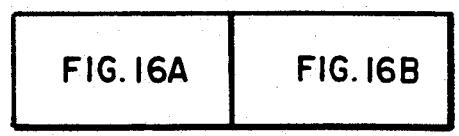

FIG. 16 illustrates the wiring diagram and channel selection capabilities of the peristaltic pump unit 42 described above. By appropriate control of the individual pumps of the array in time sequence with the rest of the test parameters, the appropriate reaction chamber can be fed with desired reagents in proper time sequence under the control of the microprocessors of FIGS. 9A and 9B operating under the instructions supplied by the computer while executing the desired test parameters.

Figure 17:
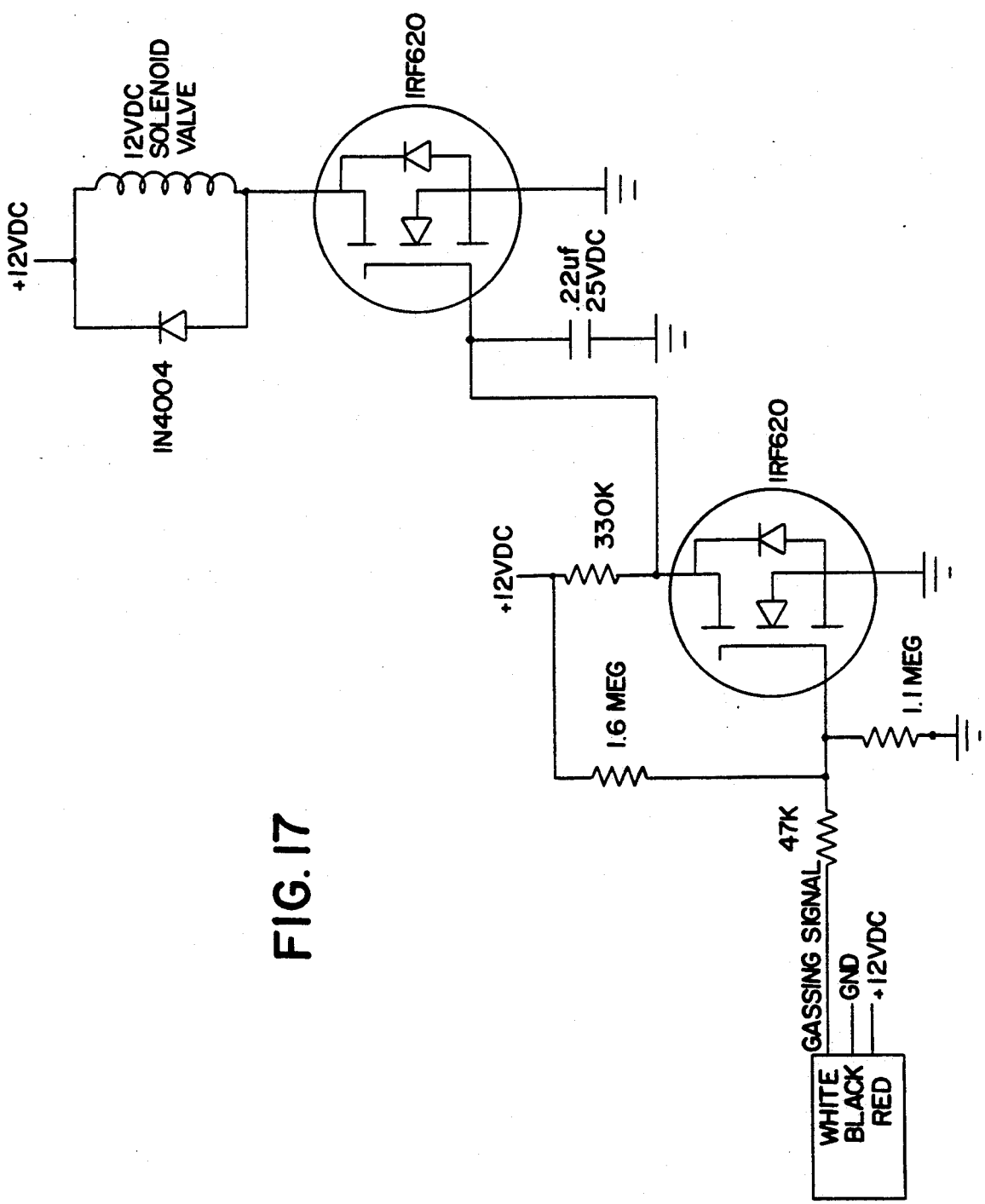
FIG. 17 is a schematic wiring diagram illustrating the control of the gassing solenoid.
Figure 18A:
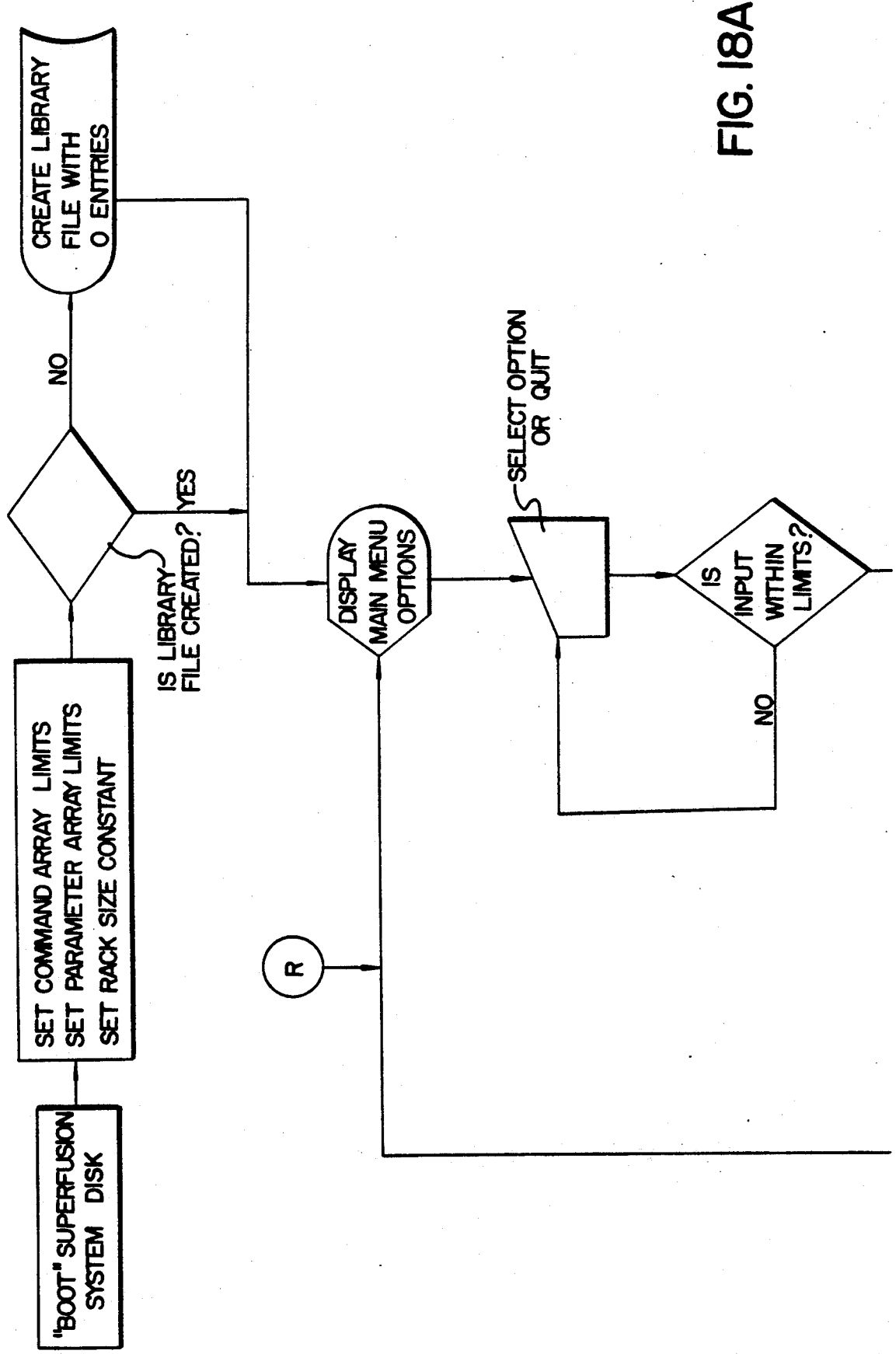
FIGS. 18, 19A to 19F and 20 to 24 are logical flow diagrams illustrating a preferred embodiment of the automated operation of the superfusion device of the invention.
Figure 18B:
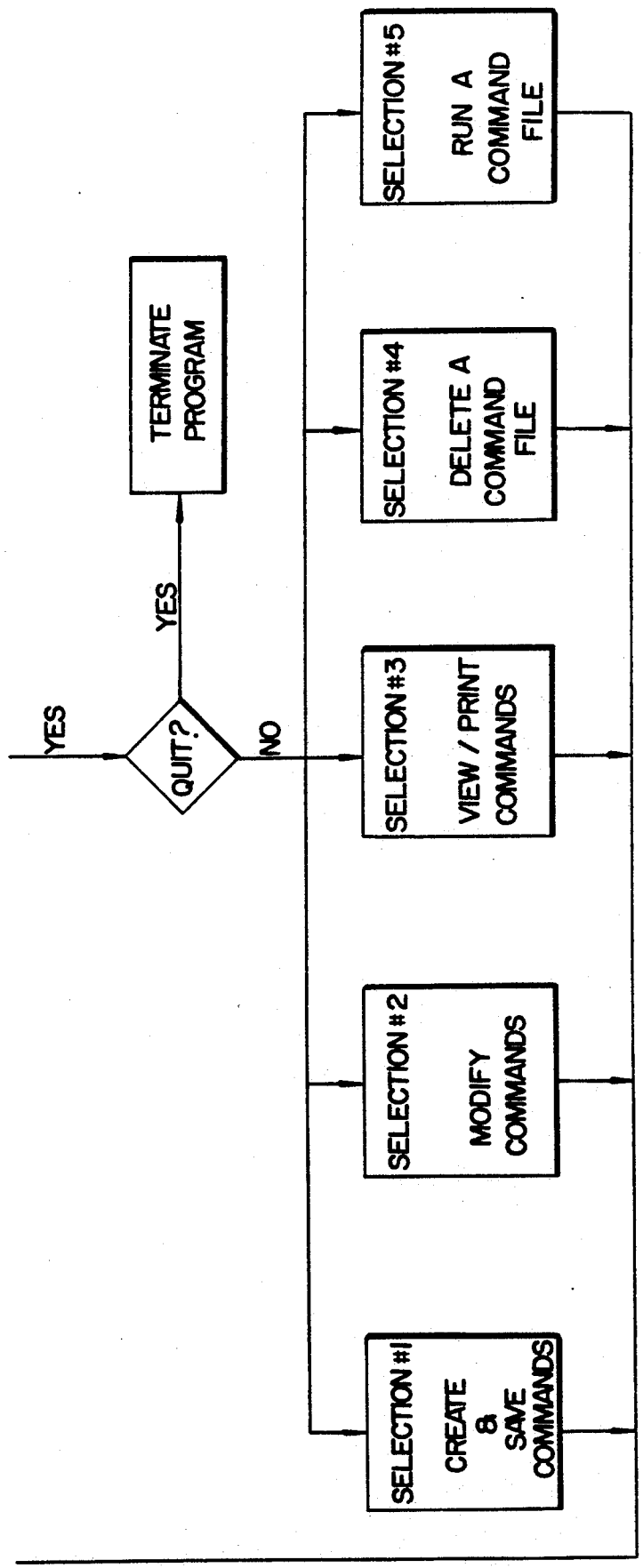

FIG. 17 illustrates the circuits for control of the solenoids for gassing of the appropriate reaction chambers when desired. The solenoids allow gas flow in and out of gas inlet and outlet ports 92 and 94 respectively FIG. 8 when necessary for the performance of a desired test. These solenoids, as before are under control of the microprocessors of FIGS. 9A and 9B and are called upon as required in the testing parameters set up and supplied to the microcontrollers.

Figure 4:
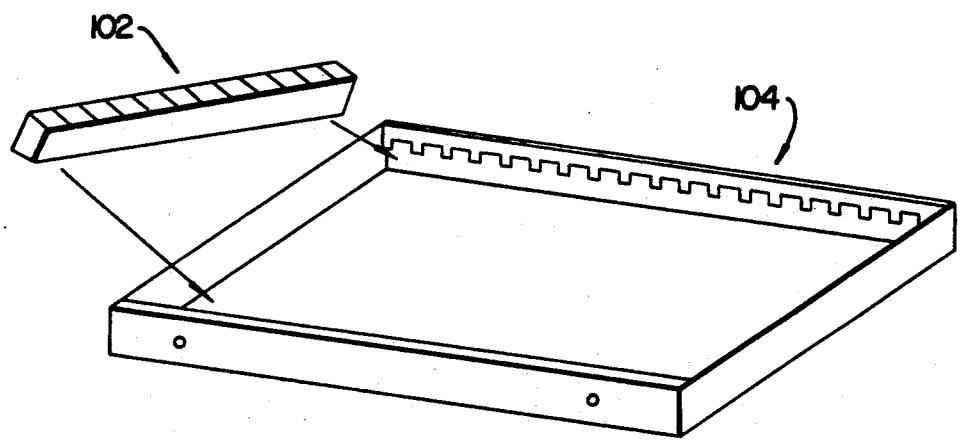
FIG. 4 is a perspective view of the scintillation rack and scintillation rack holding tray.

FIG. 4 illustrates the placement of a scintillation rack 102 which holds a row of collection vials not illustrated into place and scintillation rack holding tray 104.

Because many varying and different embodiments may be made within the scope of the inventive concept herein taught, and because many modifications may be made in the embodiments herein detailed in accordance with the descriptive requirements of the law, it is to be understood that the details herein are to be interpreted as illustrative and not in a limiting sense.

What is claimed is:

1. A perfusion device for the analysis of samples comprising:
   (a) a housing having means for controlling the temperature of said housing;
   (b) an opening in said housing;
   (c) a sample reaction chamber having a first end and a second end and a configuration for fitting inside said opening in said housing;
   (d) a sample reaction chamber plug having a first end and a second end and a passage connecting said first end with said second end and sealing means at said first end for engaging and providing a fluid tight seal between said sample reaction chamber plug and said first end of said sample reaction chamber; and
   (e) electrical stimulation means disposed in said first end of said sample reaction chamber plug.

2. The perfusion device of claim 1 wherein said electrical stimulation means is a platinum electrode.

3. The perfusion device of claim 1 wherein said first end of said sample reaction chamber includes means for removably engaging said sample reaction chamber from said opening in said housing.

4. The perfusion device of claim 3 wherein said means for removably engaging said sample reaction chamber from said opening is two notches in said first end of said sample reaction chamber.

5. The perfusion device of claim 1 further comprising a second sample reaction chamber plug having a first end and a second end and a passage connecting said first end with said second end and sealing means at said first end for providing a fluid tight seal between said second sample reaction chamber plug and said sample reaction chamber.

6. The perfusion device of claim 5 further comprising electrical stimulation means disposed in said first end of said second sample reaction chamber plug.

7. The perfusion device of claim 5 wherein said first end of said sample reaction chamber includes means for selectively removing said sample reaction chamber on said first or on said second sample reaction chamber plug.

8. The perfusion device of claim 7 wherein said means for selectively removing said sample reaction chamber is two notches in said first end of said sample reaction chamber.

9. The perfusion device of claim 5 wherein said passage connecting said first end and said second end of said first and said second sample reaction chamber plug is connected through tubing to a peristaltic pump.

10. A device for the analysis of biological samples comprising:
    (a) a housing having means for controlling the temperature of said housing;
    (b) a plurality of openings in said housing;
    (c) a plurality of substantially hollow reaction chambers having ends and an outside configuration suitable for fitting inside said plurality of openings in said housing;
    (d) a plurality of reaction chamber plugs each having a first end and a second end and a passage connecting said first end with said second end and means for sealing said first end to an end of one of said plurality of substantially hollow reaction chambers; and
    (e) pump means for pumping fluids through said passage in said plurality of reaction chamber plugs and said plurality of substantially hollow reaction chambers.

11. The device of claim 10 wherein one of the ends of said plurality of substantially hollow reaction chambers includes means for removably engaging said sample reaction chamber from said plurality of openings in said housing.

12. The device of claim 11 further comprising electrical stimulation means disposed in said first end of said plurality of reaction chamber plugs.

13. The device of claim 11 further comprising a plurality of tubing having an intake end and a discharge end connected to said pump means and moveable trays for supporting test tubes at said intake end of said discharge end of said tubing.

14. The device of claim 13 further comprising means for introducing gasses to said intake end of said tubing.

15. The device of claim 13 further comprising computer control means for moving said moveable trays.

16. The device of claim 13 further comprising means for controlling the temperature of said test tubes at said intake end and said discharge end of said tubing.

17. A superfusion device for treating biological samples comprising:
    (a) a housing having means for controlling the temperature of said housing;
    (b) a plurality of openings in said housing;
    (c) a plurality of substantially hollow reaction chambers having ends and an outside configuration suitable for fitting inside said plurality of openings in said housing;
    (d) a plurality of reaction chamber plugs each having a first end and a second end and a passage connecting said first end with said second end and means for electrical stimulation disposed in said first end; and
    (e) a peristaltic pump for pumping fluids through said passage in said plurality of reaction chamber plugs and said plurality of substantially hollow reaction chambers.

18. The superfusion device of claim 17 further comprising a plurality of tubing having an intake end and a discharge end connected to said peristaltic pump and moveable trays disposed at said intake end and said discharge end of said tubing.

19. The superfusion device of claim 18 further comprising computer control means for controlling said means for controlling the temperature of said housing and for controlling the movement of said moveable trays.

20. The superfusion device of claim 18 wherein said peristaltic pump is capable of forward and reverse pumping.